US007873173B2

(12) United States Patent
Inoue et al.

(10) Patent No.: US 7,873,173 B2
(45) Date of Patent: Jan. 18, 2011

(54) ACTIVE VIBRATORY NOISE CONTROL APPARATUS

(75) Inventors: Toshio Inoue, Tochigi-ken (JP); Akira Takahashi, Tochigi-ken (JP)

(73) Assignee: Honda Motor Co., Ltd., Tokyo (JP)

( * ) Notice: Subject to any disclaimer, the term of this patent is extended or adjusted under 35 U.S.C. 154(b) by 1182 days.

(21) Appl. No.: 11/223,950

(22) Filed: Sep. 13, 2005

(65) Prior Publication Data

US 2006/0056642 A1 Mar. 16, 2006

(30) Foreign Application Priority Data

Sep. 14, 2004 (JP) ............................ 2004-266787

(51) Int. Cl.
*A61F 11/06* (2006.01)

(52) U.S. Cl. .................. 381/71.4; 381/71.11; 381/71.1; 381/71.8; 331/10; 331/25

(58) Field of Classification Search .................. 381/71, 381/71.1, 71.4, 71.8–71.14, 97; 364/574, 364/463, 572, 421; 331/10, 25
See application file for complete search history.

(56) References Cited

U.S. PATENT DOCUMENTS 4,857,867 A * 8/1989 Griffith ........................ 331/10
4,878,188 A * 10/1989 Ziegler, Jr. .................. 708/300
5,170,433 A 12/1992 Elliott et al.
5,377,276 A 12/1994 Terai et al.
5,544,080 A * 8/1996 Kobayashi et al. .......... 700/280
5,850,458 A * 12/1998 Tomisawa et al. .......... 381/71.4
6,094,601 A 7/2000 Popovich
6,216,047 B1 4/2001 Goto
6,845,162 B1 * 1/2005 Emborg et al. ............. 381/71.4
7,062,049 B1 6/2006 Inoue et al.
2004/0240678 A1 * 12/2004 Nakamura et al. ....... 381/71.11
2004/0247137 A1 * 12/2004 Inoue et al. ................ 381/71.4

FOREIGN PATENT DOCUMENTS

EP 0396666 B1 * 3/1996 .................... 17/10
EP 1 257 997 B1 11/2002
EP 1257997 B1 * 3/2004 .................. 11/178
EP 1 515 304 A2 3/2005
JP 1-501344 5/1989
JP 05-289679 11/1993
JP 06-051787 A 2/1994
JP 06-118970 4/1994
JP 06-222779 8/1994

(Continued)

*Primary Examiner*—Vivian Chin
*Assistant Examiner*—Friedrich Fahnert
(74) *Attorney, Agent, or Firm*—Arent Fox LLP

(57) ABSTRACT

A cosine wave over one period is stored as waveform data in a memory, and address shift values based on a phase lag in transfer characteristics from a speaker to a microphone are stored in a memory. An address shift value is read from the memory by referring to the frequency, and waveform data are read from the memory at addresses that are produced by shifting the addresses from which the reference cosine wave signal and the reference sine wave signal are read, by the address shift value. The read waveform data are used as a first reference signal and a second reference signal, which are applied to adaptive notch filters, to suppress vibratory noise.

3 Claims, 17 Drawing Sheets

FOREIGN PATENT DOCUMENTS

| | | | | |
|---|---|---|---|---|
| JP | 06-236188 | A | | 8/1994 |
| JP | 06-282273 | | | 10/1994 |
| JP | 07-287586 | | | 10/1995 |
| JP | 08-006573 | | | 1/1996 |
| JP | 08-297493 | A | | 11/1996 |
| JP | 08-339191 | A | | 12/1996 |
| JP | 11-149291 | | | 6/1999 |
| JP | 2000-099037 | | | 4/2000 |
| JP | 2000-99037 | A | * | 4/2000 |
| JP | 2001-140974 | A | | 5/2001 |
| JP | 2004-361721 | | | 12/2004 |
| WO | 88/02912 | | | 4/1988 |

* cited by examiner

| ADDRESS | WAVEFORM DATA |
|---|---|
| 0 | 0 |
| 1 | $A\sin(360° \times \frac{1}{N})$ |
| ••• | ••• |
| i | $A\sin(360° \times \frac{i}{N})$ |
| ••• | ••• |
| N−1 | $A\sin(360° \times \frac{N-1}{N})$ |

FIG. 9A
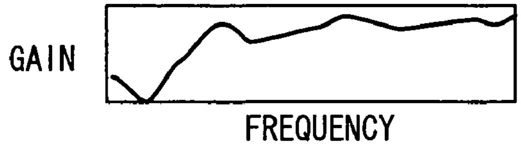
FIG. 9B
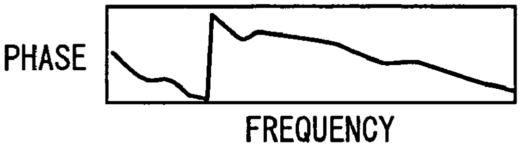
FIG. 9C
| f | GAIN (dB) | PHASE LAG |
|---|---|---|
| 30 | -30 | 328.2 |
| · | · | · |
| 40 | -28 | 348.8 |
| 41 | -20 | 359.7 |
| 42 | -10 | 6.6 |
| 43 | -6 | 15.2 |
| · | · | · |
| · | · | · |
| 200 | -12 | 146.2 |
| · | · | · |
| 230 | -8 | 256.1 |
FIG. 9D
| MEMORY 23 | |
|---|---|
| f | ADDRESS SHIFT VALUE |
| 30 | 3282 |
| · | · |
| 40 | 3488 |
| 41 | 3597 |
| 42 | 66 |
| 43 | 152 |
| · | · |
| · | · |
| 200 | 1462 |
| · | · |
| 230 | 2561 |
FIG. 9E
| GAIN SETTING UNITS 26, 27 | |
|---|---|
| f | $\alpha=127\times A$ |
| 30 | 4.016 |
| · | · |
| 40 | 5.056 |
| 41 | 12.700 |
| 42 | 40.161 |
| 43 | 63.651 |
| · | · |
| · | · |
| 200 | 31.901 |
| · | · |
| 230 | 50.560 |

FIG. 13A
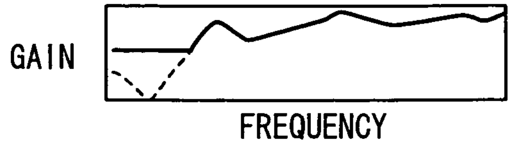
FIG. 13B
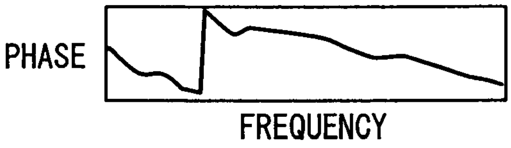
FIG. 13C
| f | GAIN (dB) | PHASE LAG |
|---|---|---|
| 30 | −10 | 328. 2 |
| · | · | · |
| 40 | −10 | 348. 8 |
| 41 | −10 | 359. 7 |
| 42 | −10 | 6. 6 |
| 43 | −6 | 15. 2 |
| · | · | · |
| · | · | · |
| 200 | −12 | 146. 2 |
| · | · | · |
| 230 | −8 | 256. 1 |
FIG. 13D
| MEMORY 23 | |
|---|---|
| f | ADDRESS SHIFT VALUE |
| 30 | 3282 |
| · | · |
| 40 | 3488 |
| 41 | 3598 |
| 42 | 66 |
| 43 | 152 |
| · | · |
| · | · |
| 200 | 1462 |
| · | · |
| 230 | 2561 |
FIG. 13E
| GAIN SETTING UNITS 26, 27 | |
|---|---|
| f | $\alpha$=127×A |
| 30 | 40. 161 |
| · | · |
| 40 | 40. 161 |
| 41 | 40. 161 |
| 42 | 40. 161 |
| 43 | 63. 651 |
| · | · |
| · | · |
| 200 | 31. 901 |
| · | · |
| 230 | 50. 560 |

FIG. 14A
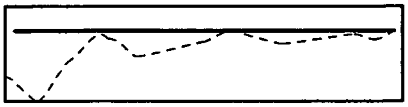
FIG. 14B
FIG. 14C
| f | GAIN (dB) | PHASE LAG |
|---|---|---|
| 30 | 0 | 328.2 |
| · | · | · |
| 40 | 0 | 348.8 |
| 41 | 0 | 359.7 |
| 42 | 0 | 6.6 |
| 43 | 0 | 15.2 |
| · | · | · |
| · | · | · |
| 200 | 0 | 146.2 |
| · | · | · |
| 230 | 0 | 256.1 |
FIG. 14D
| MEMORY 23 | |
|---|---|
| f | ADDRESS SHIFT VALUE |
| 30 | 3282 |
| · | · |
| 40 | 3488 |
| 41 | 3597 |
| 42 | 66 |
| 43 | 152 |
| · | · |
| · | · |
| 200 | 1462 |
| · | · |
| 230 | 2561 |
FIG. 14E
| GAIN SETTING UNITS 26, 27 | |
|---|---|
| f | $\alpha = 127 \times A$ |
| 30 | 127.00 |
| · | · |
| 40 | 127.00 |
| 41 | 127.00 |
| 42 | 127.00 |
| 43 | 127.00 |
| · | · |
| · | · |
| 200 | 127.00 |
| · | · |
| 230 | 127.00 |

ACTIVE VIBRATORY NOISE CONTROL APPARATUS

CROSS-REFERENCE TO RELATED APPLICATION

This application claims the priority of JP Application No. 2004-266787, filed Sep. 14, 2004, the entire specification, claims and drawings of which are incorporated herewith by reference.

BACKGROUND OF THE INVENTION

1. Field of the Invention

The present invention relates to an active vibratory noise control apparatus for actively controlling vibratory noise using adaptive notch filters, the active vibratory noise control apparatus being adapted for use in motor vehicles.

2. Description of the Related Art

Heretofore, it has been general practice in the field of active vibratory noise control in vehicle passenger compartments to model signal transfer characteristics to be controlled with a FIR filter, supply the FIR filter with input pulses based on the engine rotational speed and suspension vibration outputs that are highly correlated to vibratory noise to be controlled, use an output signal from the FIR filter as a reference signal, adaptively generate a signal to produce canceling vibratory noise for reducing an error signal from the reference signal and the error signal, and apply the generated signal to an actuator to produce secondary vibratory noise to reduce the vibratory noise.

According to an example of the above active vibratory noise control process, a reference wave signal is generated by a reference wave signal generator in response to an engine rotational speed signal, the generated reference wave signal is applied to an adaptive FIR filter, which produces an output signal to drive a speaker. The difference between vibratory noise caused in a vehicle passenger compartment by the output energy radiated from the speaker and vibratory noise produced in the vehicle passenger compartment by engine rotation, etc. is detected by a microphone installed in the vehicle passenger compartment, and the adaptive FIR filter is controlled to reduce an output signal from the microphone (see, for example, Japanese Laid-Open Patent Publication No. 1-501344 (PCT application)).

Another example is known as an active vibratory noise control apparatus employing adaptive notch filters, as shown in FIG. 17 of the accompanying drawings. This active vibratory noise control apparatus is based on the fact that vibratory noise in a vehicle passenger compartment is generated in synchronism with the rotation of the output shaft of the engine. The vibratory noise that is produced in the vehicle passenger compartment at a frequency based on the rotation of the output shaft of the engine is silenced using the adaptive notch filters.

In the known active vibratory noise control apparatus employing adaptive notch filters, as shown in FIG. 17, engine pulses which are synchronous with the rotation of the output shaft of the engine are shaped in waveform by a waveform shaper 71, whose output signal is applied to a cosine wave generator 72 and a sine wave generator 73 which generate a cosine wave signal and a sine wave signal, respectively. The cosine wave signal is passed through an adaptive notch filter 74, and the sine wave signal is passed through an adaptive notch filter 75. Output signals from the adaptive notch filters 74, 75 are added by an adder 76 into a sum signal, which is applied to energize a secondary vibratory noise generator 77.

The cosine wave signal is applied to a transfer element 78 having passenger-compartment signal transfer characteristics ($\gamma 0$) for the frequency in synchronism with the rotation of the engine output shaft, and the sine wave signal is applied to a transfer element 79 having passenger-compartment signal transfer characteristics ($\gamma 1$) for the frequency in synchronism with the rotation of the engine output shaft. Output signals from the transfer elements 78, 79 are added into a first reference signal by an adder 80. The sine wave signal is applied to a transfer element 81 having the passenger-compartment signal transfer characteristics ($\gamma 0$), and the cosine wave signal is applied to a transfer element 82 having passenger-compartment signal transfer characteristics ($-\gamma 1$). Output signals from the transfer elements 81, 82 are added into a second reference signal by an adder 83. The filter coefficients of the adaptive notch filter 74 are updated according to an adaptive algorithm based on the first reference signal, and the filter coefficients of the adaptive notch filter 75 are updated according to an adaptive algorithm based on the second reference signal, so that an error signal detected by an error detecting means 86 will be minimized. For details, reference should be made to Japanese Laid-Open Patent Publication No. 2000-99037, for example.

The above example of the active vibratory noise control process which employs an FIR filter for producing a reference signal (for example, Japanese Laid-Open Patent Publication No. 1-501344 (PCT application)) is problematic in that because of convolutional calculations to be done by the FIR filter, if the active vibratory noise control process is to cancel passenger-compartment vibratory noise at rapid accelerations of the vehicle, the sampling frequency needs to be increased, and the number of taps of the FIR filter also needs to be increased, with the results that the processing load on the FIR filter is large, and an active vibratory noise control apparatus for performing the active vibratory noise control process requires a processor having a large processing capability, such as a digital signal processor, and hence is highly expensive.

The active vibratory noise control apparatus employing adaptive notch filters (for example, Japanese Laid-Open Patent Publication No. 2000-99037) is disadvantageous in that though the amount of calculations required to produce reference signals may be small, the signal transfer characteristics from the secondary vibratory noise generator to the error signal detecting means is not sufficiently optimally modeled, and optimum reference signals for updating the filter coefficients of the adaptive notch filters are not obtained, with the results that the active vibratory noise control apparatus may find it difficult to cancel passenger-compartment vibratory noise at rapid accelerations of the vehicle and fail to provide a sufficient vibratory noise control capability.

The applicant of the present application has proposed an active vibratory noise control apparatus having a storage device having a memory for storing a cosine corrective value, in association with a control frequency, based on the cosine value of a phase lag in the signal transfer characteristics between a speaker and a microphone, and a memory for storing a sine corrective value, in association with the control frequency, based on the sine value of the phase lag in the signal transfer characteristics between the speaker and the microphone. The cosine corrective value read from the storage device and a reference cosine signal output from a cosine wave generating circuit are multiplied by each other, and the sine corrective value read from the storage device and a reference sine signal output from a sine wave generating circuit are multiplied by each other. The product signals are processed into a first reference signal. The cosine corrective value read from the storage device and the reference sine signal output from the sine wave generating circuit are multiplied by each other, and the sine corrective value read from the storage device and the reference cosine signal output from a cosine wave generating circuit are multiplied by each other. The product signals are processed into a second reference signal. For details, reference should be made to Japanese Laid-Open Patent Publication No. 2004-361721. The applicant of the present application is one of the co-applicants of Japanese Laid-Open Patent Publication No. 2004-361721.

SUMMARY OF THE INVENTION

It is an object of the present invention to provide an active vibratory noise control apparatus which performs a reduced amount of processing for producing reference signals and which has a sufficient vibratory noise controlling capability.

An apparatus for actively controlling vibratory noise according to an aspect of the present invention includes reference wave signal generating means for outputting a reference wave signal having a harmonic frequency selected from frequencies of vibration or noise generated from a vibratory noise source; an adaptive notch filter for outputting a control signal based on the reference wave signal in order to cancel vibratory noise; vibratory noise canceling means for generating a vibratory noise canceling sound based on the control signal; error signal detecting means for outputting an error signal based on a difference between the vibration or noise and the vibratory noise canceling sound; correcting means for correcting the reference wave signal into a reference signal based on a corrective value representing phase characteristics with respect to a frequency of the reference wave signal in transfer characteristics from the vibratory noise canceling means to the error signal detecting means, and outputting the reference signal; and filter coefficient updating means for sequentially updating a filter coefficient of the adaptive notch filter in order to minimize the error signal based on the error signal and the reference signal; wherein the reference wave signal generating means has waveform data storage means for storing waveform data representing instantaneous value data at respective divided positions where one period of a sine wave or a cosine wave is divided by a predetermined number, and successively reads the waveform data from the waveform data storage means per sampling to generate the reference wave signal; and wherein the correcting means has corrective data storage means for storing the corrective value with respect to the frequency of the reference wave signal, and the correcting means reads the corrective value from the corrective data storage means by referring to the frequency of the reference wave signal, shifts an address at which the reference wave signal generating means reads the waveform data from the waveform data storage means, by the corrective value, and reads the waveform data from the shifted address of the waveform data storage means as the reference signal.

As described above, the apparatus for actively controlling vibratory noise according to the aspect of the present invention has the waveform data storage means and the corrective data storage means. Waveform data are read as the reference wave signal from the waveform data storage means per sampling. At the same time, the frequency of the reference wave signal is referred to, and the corrective value is read from the corrective data storage means. Waveform data are read as the reference signal from the address produced by shifting the address at which the waveform data are read from the waveform data storage means, by the corrective value read from the corrective data storage means.

Since the waveform data are read as the reference signal from the address of the waveform data storage means which is produced by shifting the address at which the reference wave signal is read from the waveform data storage means, by the corrective value read from the corrective data storage means, it is not necessary to employ an FIR filter and to perform convolutional calculations in order to obtain a reference signal as with the conventional apparatus. The amount of calculations to obtain a reference signal may be greatly reduced, and even an inexpensive microcomputer may be used without impairing control responsiveness. Therefore, the apparatus for actively controlling vibratory noise can be constructed inexpensively.

An apparatus for actively controlling vibratory noise according to another aspect of the present invention includes reference wave signal generating means for outputting a reference sine wave signal and a reference cosine wave signal having a harmonic frequency selected from frequencies of vibration or noise generated from a vibratory noise source; a first adaptive notch filter for outputting a first control signal based on the reference cosine wave signal and a second adaptive notch filter for outputting a second control signal based on the reference sine wave signal in order to cancel generated vibratory noise; vibratory noise canceling means for generating a vibratory noise canceling sound based on a sum signal representing the sum of the first control signal and the second control signal; error signal detecting means for outputting an error signal based on a difference between the vibration or noise and the vibratory noise canceling sound; correcting means for correcting the reference cosine wave signal into a first reference signal and correcting the reference sine wave signal into a second reference signal, based on a corrective value representing phase characteristics with respect to a frequency of each of the reference cosine wave signal and the reference sine wave signal in transfer characteristics from the vibratory noise canceling means to the error signal detecting means, and outputting the first reference signal and the second reference signal; and filter coefficient updating means for sequentially updating a filter coefficient of the first adaptive notch filter and a filter coefficient of the second adaptive notch filter in order to minimize the error signal based on the error signal, the first reference signal, and the second reference signal; wherein the reference wave signal generating means has waveform data storage means for storing waveform data representing instantaneous value data at respective divided positions where one period of a cosine wave is divided by a predetermined number, and the reference wave signal generating means successively reads the waveform data from the waveform data storage means per sampling to generate the reference cosine wave signal, and successively reads the waveform data from addresses of the waveform data storage means which are produced by shifting addresses at which the reference cosine signal is read, by a quarter of the period, to generate the reference sine wave signal; and wherein the correcting means has corrective data storage means for storing the corrective value with respect to the frequency of the reference wave signal, and the correcting means reads the corrective value from the corrective data storage means by referring to the frequency of the reference wave signal, shifts an address at which the reference wave signal generating means reads the waveform data as the reference cosine wave signal from the waveform data storage means, by the corrective value, reads the waveform data from the shifted address of the waveform data storage means as the first reference signal, shifts an address at which the reference wave signal generating means reads the waveform data as the reference sine wave signal from the waveform data storage means, by the corrective value, and reads the waveform data from the shifted address of the waveform data storage means as the second reference signal.

As described above, the apparatus for actively controlling vibratory noise according to the other aspect of the present invention has the waveform data storage means and the corrective data storage means. Waveform data are successively read as the reference cosine wave signal from the waveform data storage means per sampling, and waveform data are successively read as the reference sine wave signal from addresses of the waveform data storage means which are produced by shifting the addresses at which the reference cosine signal is read, by a quarter of the period.

Because two reference wave signals (the reference sine wave signal and the reference cosine wave signal) can be generated from one waveform data storage means, the storage capacity of the waveform data storage means may be reduced, and an inexpensive microcomputer may be employed.

At the same time, the frequency of the reference wave signal is referred to, and the corrective value is read from the corrective data storage means. Waveform data are read as the first reference signal from the address produced by shifting the address at which the waveform data for the reference cosine wave signal are read from the waveform data storage means, by the corrective value read from the corrective data storage means. Waveform data are read as the second reference signal from the address produced by shifting the address at which the waveform data for the reference sine wave signal are read from the waveform data storage means, by the corrective value read from the corrective data storage means.

With the apparatus for actively controlling vibratory noise according to the other aspect of the present invention, it is not necessary to employ an FIR filter and to perform convolutional calculations in order to obtain first and second reference signals as with the conventional apparatus. The amount of calculations to obtain reference signals may be greatly reduced, and even an inexpensive microcomputer may be used without impairing control responsiveness. Therefore, the apparatus for actively controlling vibratory noise can be constructed inexpensively.

Furthermore, with the apparatus for actively controlling vibratory noise according to the other aspect of the present invention, the first and second reference signals which accurately reflect the transfer characteristics of vibration or noise having frequencies to be controlled are easily obtained from the waveform data read from the waveform data storage means which refers to the corrective value read from the corrective data storage means, making it possible to suppress vibratory noise accurately. As described above, inasmuch as the first and second reference signals are obtained as optimally corrected signals from the reference wave signals, the contours of constant square error curves become concentric circles, converging the cancellation of generated vibratory noise quickly.

An apparatus for actively controlling vibratory noise according to still another aspect of the present invention includes reference wave signal generating means for outputting a reference sine wave signal and a reference cosine wave signal having a harmonic frequency selected from frequencies of vibration or noise generated from a vibratory noise source; a first adaptive notch filter for outputting a first control signal based on the reference cosine wave signal and a second adaptive notch filter for outputting a second control signal based on the reference sine wave signal in order to cancel generated vibratory noise; vibratory noise canceling means for generating a vibratory noise canceling sound based on a sum signal representing the sum of the first control signal and the second control signal; error signal detecting means for outputting an error signal based on a difference between the vibration or noise and the vibratory noise canceling sound; correcting means for correcting the reference cosine wave signal into a first reference signal and correcting the reference sine wave signal into a second reference signal, based on a corrective value representing phase characteristics with respect to a frequency of each of the reference cosine wave signal and the reference sine wave signal in transfer characteristics from the vibratory noise canceling means to the error signal detecting means, and outputting the first reference signal and the second reference signal; and filter coefficient updating means for sequentially updating a filter coefficient of the first adaptive notch filter and a filter coefficient of the second adaptive notch filter in order to minimize the error signal based on the error signal, the first reference signal, and the second reference signal; wherein the reference wave signal generating means has waveform data storage means for storing waveform data representing instantaneous value data at respective divided positions where one period of a sine wave is divided by a predetermined number, and the reference wave signal generating means successively reads the waveform data from the waveform data storage means per sampling to generate the reference sine wave signal, and successively reads the waveform data from addresses of the waveform data storage means which are produced by shifting addresses at which the reference sine signal is read, by a quarter of the period, to generate the reference cosine wave signal; and wherein the correcting means has corrective data storage means for storing the corrective value with respect to the frequency of the reference wave signal, and the correcting means reads the corrective value from the corrective data storage means by referring to the frequency of the reference wave signal, shifts an address at which the reference wave signal generating means reads the waveform data as the reference sine wave signal from the waveform data storage means, by the corrective value, reads the waveform data from the shifted address of the waveform data storage means as the second reference signal, shifts an address at which the reference wave signal generating means reads the waveform data as the reference cosine wave signal from the waveform data storage means, by the corrective value, and reads the waveform data from the shifted address of the waveform data storage means as the first reference signal.

As described above, the apparatus for actively controlling vibratory noise according to the still other aspect of the present invention has the waveform data storage means and the corrective data storage means. Waveform data are successively read as the reference sine wave signal from the waveform data storage means per sampling, and waveform data are successively read as the reference cosine wave signal from addresses of the waveform data storage means which are produced by shifting the addresses at which the reference sine signal is read, by a quarter of the period.

Because two reference wave signals (the reference sine wave signal and the reference cosine wave signal) can be generated from one waveform data storage means, the storage capacity of the waveform data storage means may be reduced, and an inexpensive microcomputer may be employed.

At the same time, the frequency of the reference wave signal is referred to, and the corrective value is read from the corrective data storage means. Waveform data are read as the second reference signal from the address produced by shifting the address at which the waveform data for the reference cosine wave signal are read from the waveform data storage means, by the corrective value read from the corrective data storage means. Waveform data are read as the first reference signal from the address produced by shifting the address at which the waveform data for the reference sine wave signal are read from the waveform data storage means, by the corrective value read from the corrective data storage means.

With the apparatus for actively controlling vibratory noise according to the still other aspect of the present invention, it is not necessary to employ an FIR filter and to perform convolutional calculations in order to obtain first and second reference signals as with the conventional apparatus. The amount of calculations to obtain reference signals may be greatly reduced, and even an inexpensive microcomputer may be used without impairing control responsiveness. Therefore, the apparatus for actively controlling vibratory noise can be constructed inexpensively.

Furthermore, with the apparatus for actively controlling vibratory noise according to the still other aspect of the present invention, the first and second reference signals which accurately reflect the transfer characteristics of vibration or noise having frequencies to be controlled are easily obtained from the waveform data read from the waveform data storage means which refers to the corrective value read from the corrective data storage means, making it possible to suppress vibratory noise accurately. As described above, inasmuch as the first and second reference signals are obtained as optimally corrected signals from the reference wave signals, the contours of constant square error curves become concentric circles, converging the cancellation of generated vibratory noise quickly.

The above and other objects, features, and advantages of the present invention will become more apparent from the following description when taken in conjunction with the accompanying drawings in which preferred embodiments of the present invention are shown by way of illustrative example.

BRIEF DESCRIPTION OF THE DRAWINGS

FIGS. 9A through 9E are diagrams showing address shift values in the system in which the active vibratory noise control apparatus according to the embodiment of the present invention is incorporated in the motor vehicle;

FIGS. 13A through 13E are diagrams showing address shift values in the system in which the active vibratory noise control apparatus according to the embodiment of the present invention is incorporated in the motor vehicle;

FIGS. 14A through 14E are diagrams showing address shift values in the system in which the active vibratory noise control apparatus according to the embodiment of the present invention is incorporated in the motor vehicle;

DESCRIPTION OF THE PREFERRED EMBODIMENTS

Active vibratory noise control apparatus according to preferred embodiments of the present invention will be described below.

Figure 1:
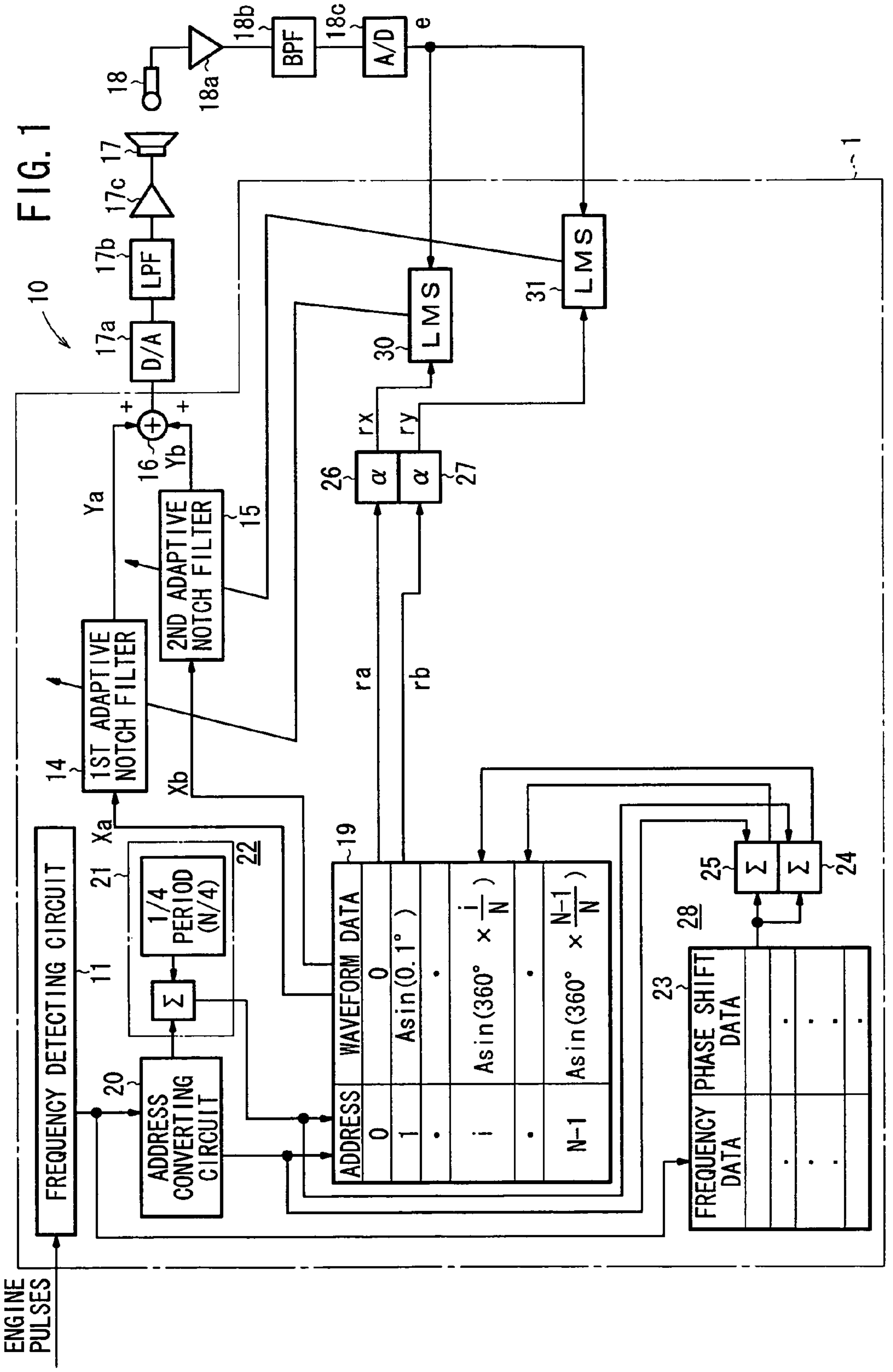
FIG. 1 is a block diagram of an active vibratory noise control apparatus according to an embodiment of the present invention.

FIG. 1 shows in block form an active vibratory noise control apparatus according to an embodiment of the present invention.

The active vibratory noise control apparatus, generally designated by 10 in FIG. 1, is arranged to cancel vibratory noise including muffled sounds of the engine on a motor vehicle, for example, which serve as main vibratory noise in the passenger compartment of the vehicle.

As shown in FIG. 1, the active vibratory noise control apparatus 10 has primary components which are functionally implemented by a microcomputer 1. The rotational speed of the output shaft of the engine is detected as engine pulses such as top-dead-center pulses by a Hall device. The detected engine pulses are supplied to a frequency detecting circuit 11 of the active vibratory noise control apparatus 10. The frequency detecting circuit 11 detects the frequency of the engine pulses from the engine pulses, and generates a signal based on the detected frequency.

The frequency detecting circuit 11 monitors engine pulses at a sampling frequency that is much higher than the frequency of the engine pulses, detects timings at which the polarity of the engine pulses changes, measures time intervals between the detected timings to detect the frequency of the engine pulses as a rotational speed of the engine output shaft, and outputs a signal having a control frequency in synchronism with the rotational speed of the engine output shaft based on the detected frequency.

Since muffled sounds of the engine are vibratory radiation sounds which are produced when excitation forces generated by the rotation of the engine output shaft are transmitted to the vehicle body, the muffled sounds of the engine are highly periodic in synchronism with the rotational speed of the engine. If the engine comprises a 4-cycle 4-cylinder engine, for example, then the engine produces excitation vibrations due to torque variations thereof upon gas combustion each time the engine output shaft makes one-half of a revolution, causing vibratory noise in the passenger compartment of the vehicle.

Since vibratory noise referred to as a rotational secondary component having a frequency which is twice the rotational speed of the engine output shaft is generated if the engine comprises a 4-cycle 4-cylinder engine, the frequency detecting circuit 11 generates and outputs a signal having a frequency which is twice the detected frequency as the control frequency. The control frequency is the frequency of vibratory noise to be canceled, and is also referred to simply as frequency.

The frequency detecting circuit 11 also generates a timing signal (sampling pulses) having the sampling period of the microcomputer 1. The microcomputer 1 performs a processing sequence such as an LMS algorithm to be described below based on the timing signal.

Figure 2:
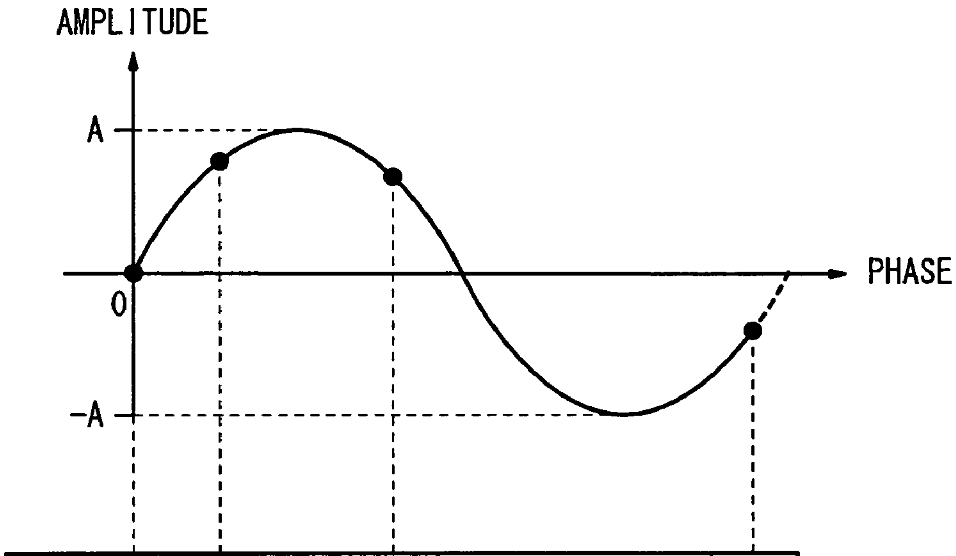
FIG. 2 is a diagram showing data stored in a memory in the active vibratory noise control apparatus according to the embodiment of the present invention.

As shown in FIG. 2, a memory 19 stores at respective addresses waveform data representing instantaneous values of the waveform of a sine wave over one period which is divided into a predetermined number (N) of equal segments along a time axis. The addresses (i) range from 0 to an integer representing (the predetermined number−1) (i=0, 1, 2, . . . , N−1). "A" shown in FIG. 2 represents 1 or any positive real number. Therefore, the waveform data at an address (i) is calculated by A sin(360°×i/N). Stated otherwise, one cycle of a sine wave is sampled by being divided by N over time, the sampling points are used as the addresses of the memory 19, and quantized data representing the instantaneous values of the sine wave at the sampling points are stored as waveform data at the respective addresses in the memory 19.

In response to the output signal from the frequency detecting circuit 11, a first address converting circuit 20 designates addresses based on the control frequency as readout addresses for the memory 19. A second address converting circuit 21 designates addresses that are shifted a quarter (¼) of the period from the addresses designated by the first address converting circuit 20, as readout addresses for the memory 19.

The memory 19 corresponds to a waveform data storage means, and the frequency detecting circuit 11, the memory 19, and the first and second address converting circuits 20, 21 jointly make up a reference wave signal generating means 22.

Figure 3A:
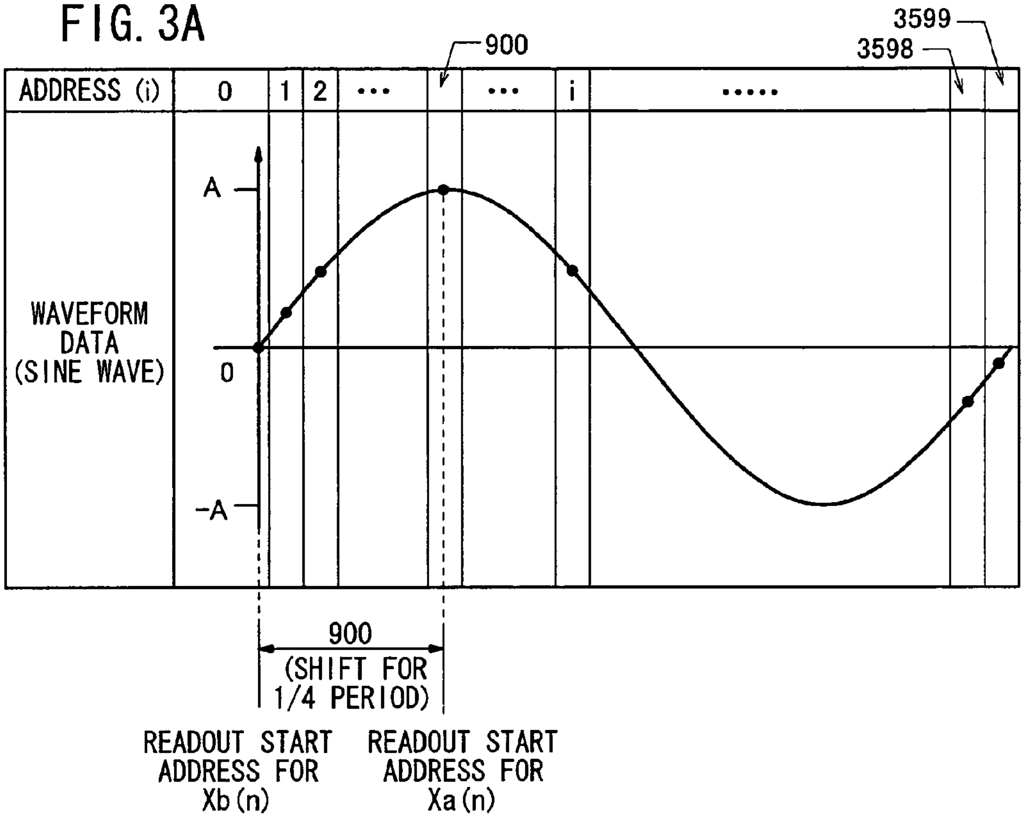
FIGS. 3A through 3C are diagrams showing the manner in which data are read from the memory in the active vibratory noise control apparatus according to the embodiment of the present invention.
Figure 3B:
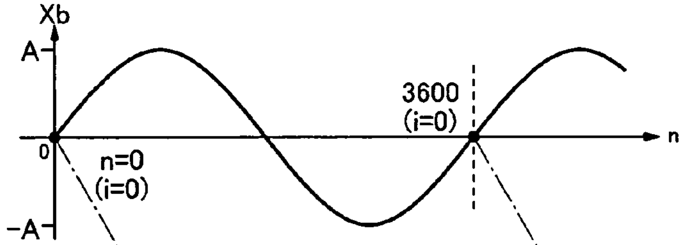
Figure 3C:
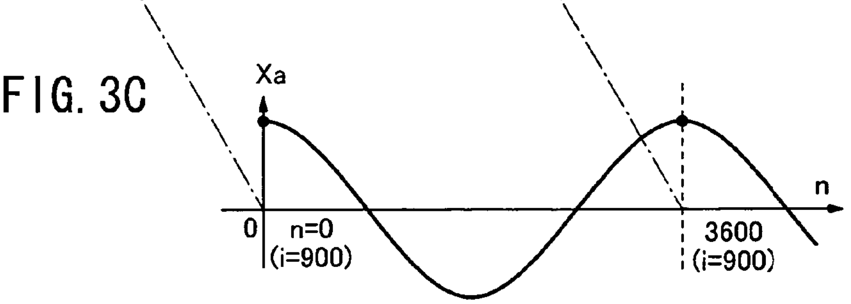

FIGS. 3A through 3C show the manner in which the reference wave signal generating means 22 generates reference wave signals including a reference cosine wave signal and a reference sine wave signal. A process in which the reference wave signal generating means 22 generates a reference cosine wave signal and a reference sine wave signal will be described below with reference to FIGS. 3A through 3C. In FIGS. 3A through 3C, "n" is an integer of 0 or greater and represents the count of sampling pulses (timing signal count). FIG. 3A shows the relationship between the addresses of the memory 19 and the waveform data. FIG. 3B shows how a reference sine wave signal is generated, and FIG. 3C shows how a reference cosine wave signal is generated.

First, a process in which a timing signal is output at a constant sampling period from the frequency detecting circuit 11 (fixed sampling process) will be described below. In the present embodiment, it is assumed that the predetermined number (N) is 3600 as shown in FIGS. 3A through 3C. Therefore, the addresses of the memory 19 are indicated as i=0, 1, 2, . . . , N−1=0, 1, 2, . . . , 3599, and the address shift represented by the quarter (¼) of the period is indicated as N/4=900. For the sake of brevity, the sampling interval (time) t=1/N=1/3600 (sec.).

Since the sampling interval is 1/3600 sec. (1/N sec.), the first address converting circuit 20 designates a readout address i(n) at an address interval based on the control frequency (f), as indicated by the equations shown below, for each sampling pulse supplied from the frequency detecting circuit 11.

Address interval "is"=N×f×t=3600×f×1/3600=f.

Therefore, an address i(n) at a certain timing is given as:

$$i(n)=i(n-1)+is=i(n-1)+f$$

When i(n)>3599 (=N−1), $$i(n)=i(n-1)+f-3600.$$

Consequently, the reference wave signal generating means 22 generates a reference sine wave signal Xb(n) by successively reading the waveform data from the memory 19 at address intervals corresponding to the control frequency for respective sampling pulses generated by the frequency detecting circuit 11. For example, if the control frequency is 40 Hz (=engine rotational speed Ne=1200 rpm), then when the control process is started, waveform data corresponding to the addresses i(n)=0, 40, 80, 120, . . . , 3560, 0, . . . for respective sampling pulses, i.e., for respective intervals of 1/3600 sec. are read from the memory 19, and a reference sine wave signal Xb(n) having a frequency of 40 Hz is generated.

The second address converting circuit 21 designates addresses that are shifted (incremented) a quarter (¼) of the period from readout addresses i(n) of the reference sine wave signal output from (designated by) the first address converting circuit 20, according to sin(θ+π/2)=cos θ as readout addresses i'(n), as indicated by the following equation:

$$i'(n)=i(n)+N/4=i(n)+900$$

When i'(n)>3599 (=N−1), i'(n)=i(n)+900−3600.

Therefore, the reference wave signal generating means 22 generates a reference cosine wave signal Xa(n) by successively reading the waveform data from the memory 19 at address intervals corresponding to the control frequency for respective sampling pulses generated by the frequency detecting circuit 11, from addresses that are shifted a quarter (¼) of the period from the addresses of the reference wave signal.

For example, if the control frequency is 40 Hz, then when the control process is started, waveform data corresponding to the addresses i'(n)=900, 940, 980, 1020, . . . , 860, 900, . . . for respective sampling pulses, i.e., for respective intervals of 1/3600 sec. are read from the memory 19, and a reference cosine wave signal Xa(n) having a frequency of 40 Hz is generated. That is, according to the fixed sampling process, the reference wave signal is generated by varying readout address intervals of waveform data depending on the control frequency.

A process in which a timing signal is output at a sampling period in synchronism with the rotational speed of the engine output shaft (the engine rotational speed) from the frequency detecting circuit 11 (synchronous sampling process or variable sampling process) will be described below. It is assumed that the predetermined number (N) is 60. Therefore, the addresses of the memory 19 are indicated as i=0, 1, 2, . . . , N−1=0, 1, 2, . . . , 59, and the address shift represented by the quarter (¼) of the period is indicated as N/4=15. Though the predetermined number (N) is of a value different from the value shown in FIGS. 3A through 3C, the synchronous sampling process is based on the same principles as the fixed sampling process.

According to the synchronous sampling process, sampling intervals vary depending on, i.e., in synchronism with, the engine rotational speed. The frequency detecting circuit 11 outputs sampling pulses at a sampling interval (time) depending on the detected control frequency (f) according to the following equation:

$$i=1/(f\times N)=1/(f\times 60)\ \text{(sec.)}$$

The first address converting circuit 20 designates a readout address i(n) by incrementing an address by 1, as indicated by the equation shown below, for each sampling pulse supplied from the frequency detecting circuit 11.

An address i(n) at a certain timing is given as:

$$i(n)=i/(n-1)+1$$

When i(n)>59 (=N−1), i(n)=i/(n−1)+1−60

Therefore, the reference wave signal generating means 22 generates a reference sine wave signal Xb(n) by successively reading the waveform data from the memory 19 for respective sampling pulses generated by the frequency detecting circuit 11, from addresses that are being incremented by 1. For example, if the control frequency is 40 Hz, then when the control process is started, waveform data corresponding to the addresses i(n)=0, 1, 2, 3, . . . , 59, 0, . . . for respective sampling pulses generated at intervals of 1/2400 sec. are read from the memory 19, and a reference sine wave signal Xb(n) having a frequency of 40 Hz is generated. If the control frequency is 50 Hz, then when the control process is started, waveform data corresponding to the addresses i(n)=0, 1, 2, 3, . . . , 59, 0, . . . for respective sampling pulses generated at intervals of 1/3000 sec. are read from the memory 19, and a reference sine wave signal Xb(n) having a frequency of 50 Hz (=engine rotational speed Ne=1500 rpm) is generated.

The second address converting circuit 21 designates addresses that are shifted (incremented) a quarter (¼) of the period from readout addresses i(n) of the reference sine wave signal output from (designated by) the first address converting circuit 20 as readout addresses i'(n), as indicated by the following equation:

$$i'(n)=i(n)+N/4=i(n)+15$$

When i'(n)>59 (=N−1), i'(n)=i(n)+15−60

Therefore, the reference wave signal generating means 22 generates a reference cosine wave signal Xa(n) by successively reading the waveform data from the memory 19 at address intervals corresponding to the control frequency for respective sampling pulses generated by the frequency detecting circuit 11, from addresses that are shifted a quarter (¼) of the period from the readout addresses.

For example, if the control frequency is 40 Hz, then when the control process is started, waveform data corresponding to the addresses i'(n)=15, 16, 17, 18, . . . , 14, 15, . . . for respective sampling pulses generated at intervals of 1/2400 sec. are read from the memory 19, and a reference cosine wave signal Xa(n) having a frequency of 40 Hz is generated. If the control frequency is 50 Hz, then when the control process is started, waveform data corresponding to the addresses i'(n)=15, 16, 17, 18, . . . , 14, 15, . . . for respective sampling pulses generated at intervals of 1/3000 sec. are read from the memory 19, and a reference sine wave signal Xa(n) having a frequency of 50 Hz is generated.

According to the synchronous sampling process, therefore, a reference wave signal is generated by varying a waveform data reading time interval depending on the control frequency.

In the above embodiment, the memory 19 stores waveform data representing instantaneous values of the waveform of a sine wave over one period which is divided into a predetermined number (N) of equal segments along a time axis. However, the memory 19 may store waveform data representing instantaneous values of the waveform of a cosine wave over one period which is divided into a predetermined number (N) of equal segments along a time axis.

In the latter case, readout addresses i(n) of the reference sine wave signal with respect to readout addresses i'(n) of the reference cosine wave signal are designated as addresses that are decremented by a quarter (¼) of the period from cos(θ−π/2)=sin(θ), according to the following equation:

$$i(n)=i'(n)-N/4$$

When i(n)<0, i(n)=i'(n)−N/4+N, and when i'(n)>N−1, i(n)=i'(n)−N/4−N.

In view of the periodic nature of each of the reference wave signals, readout addresses i(n) of the reference sine wave signal with respect to readout addresses i'(n) of the reference cosine wave signal may be designated as addresses that are incremented by three quarters (¾)of the period, according to the following equation:

$$i(n)=i'(n)+3\times N/4$$

When i'(n)>N−1, i(n)=i'(n)+3×N/4−N.

It can easily be understood that the phrase "shifted a quarter of the period" as described in claims means "incremented or decremented by a quarter of the period" and "decremented or incremented by three quarters of the period".

In the embodiment, a fixed sampling process having a predetermined number (N=3600) of sine waveform data will be described below. The phrase "per sampling" as described in claims means "for each sampling pulse (timing signal)" described in the embodiment.

The reference cosine wave signal and the reference sine wave signal thus generated serve as reference wave signals having harmonic frequencies of the frequency of the rotation of the engine output shaft, and have the frequency of vibratory noise to be canceled out, as described above.

The reference cosine wave signal is supplied to a first adaptive notch filter 14, whose filter coefficients are adaptively processed by an LMS algorithm, to be described later, and updated for each sampling pulse. The reference sine wave signal is supplied to a second adaptive notch filter 15, whose filter coefficients are adaptively processed by an LMS algorithm, to be described later, and updated for each sampling pulse. An output signal from the first adaptive notch filter 14 and an output signal from the second adaptive notch filter 15 are supplied to an adder 16, which supplies an output sum signal to an D/A converter 17*a*. The D/A converter 17*a* converts the output sum signal into an analog signal that is applied through a low-pass filter (LPF) 17*b* and an amplifier (AMP) 17*c* to a speaker 17, which outputs radiated sounds.

Therefore, the output sum signal (vibratory noise canceling signal) from the adder 16 is supplied to the speaker 17 (vibratory noise canceling means), which is installed in the passenger compartment to generate canceling vibratory noise. The speaker 17 is thus driven by the output sum signal from the adder 16. The passenger compartment houses therein a microphone 18 (error signal detecting means) for detecting remaining vibratory noise in the passenger compartment and outputting the detected remaining vibratory noise as an error signal.

The output signal from the microphone 18 is supplied through an amplifier (AMP) 18*a* and a bandpass filter (BPF) 18*b* to an A/D converter 18*c*, which converts the supplied signal into digital data that is input to LMS algorithm processors 30, 31.

The active vibratory noise control apparatus 10 also has a memory 23 as a corrective data storage means for storing address shift values which are corrective values based on a phase lag in the signal transfer characteristics between the speaker 17 and the microphone 18 with respect to respective control frequencies, i.e., address shift values with respect to the addresses of the memory 19 in association with the respective control frequencies, an adder 25 for adding an address shift value read from an address of the memory 23 which is designated based on a control frequency depending on the output signal from the frequency detecting circuit 11, and address data output from the first address converting circuit 20 into a sum value for designating an address of the memory 19, an adder 24 for adding the read address shift value and address data output from the second address converting circuit 21 into a sum value for designating an address of the memory 19, and gain setting units 26, 27 for setting a gain ratio for waveform data read from the addresses of the memory 19 which are designated by the output signals from the adders 24, 25.

The memory 23, the adders 24, 25, and the gain setting units 26, 27 jointly make up a reference signal generating circuit 28, and the reference signal generating circuit 28 and the memory 19 jointly make up a correcting means. A control frequency is referred to, and an address shift value depending on the control frequency is read from the memory 23. The address shift value and the address data output from the second address converting circuit 21 are added by the adder 24 into a sum value, and waveform data are read from the address of the memory 19 which is based on the sum value. The read waveform data are multiplied by the gain ratio, and the product signal is output as a first reference signal from the gain setting unit 26. The address shift value and the address data output from the first address converting circuit 20 are added by the adder 25 into a sum value, and waveform data are read from the address of the memory 19 which is based on the sum value. The read waveform data are multiplied by the gain ratio, and the product signal is output as a second reference signal from the gain setting unit 27. The first reference signal is a signal based on the reference cosine wave signal of the control frequency which is shifted in phase by a value based on the address shift value. The second reference signal is a signal based on the reference sine wave signal of the control frequency which is shifted in phase by a value based on the address shift value.

The first reference signal output from the gain setting unit 26 and the output signal from the microphone 18 are supplied to the LMS algorithm processor 30 and processed thereby according to an LMS algorithm thereby. The filter coefficients of the first adaptive notch filter 14 are updated per sampling pulse based on an output signal from the LMS algorithm processor 30 to minimize the output signal from the microphone 18, i.e., the error signal. The second reference signal output from the gain setting unit 27 and the output signal from the microphone 18 are supplied to the LMS algorithm processor 31 and processed thereby according to an LMS algorithm thereby. The filter coefficients of the second adaptive notch filter 15 are updated per sampling pulse based on an output signal from the LMS algorithm processor 31 to minimize the output signal from the microphone 18, i.e., the error signal.

Operation of the active vibratory noise control apparatus 10 which incorporates address shift values stored in the memory 23 will be described below.

Figure 4:
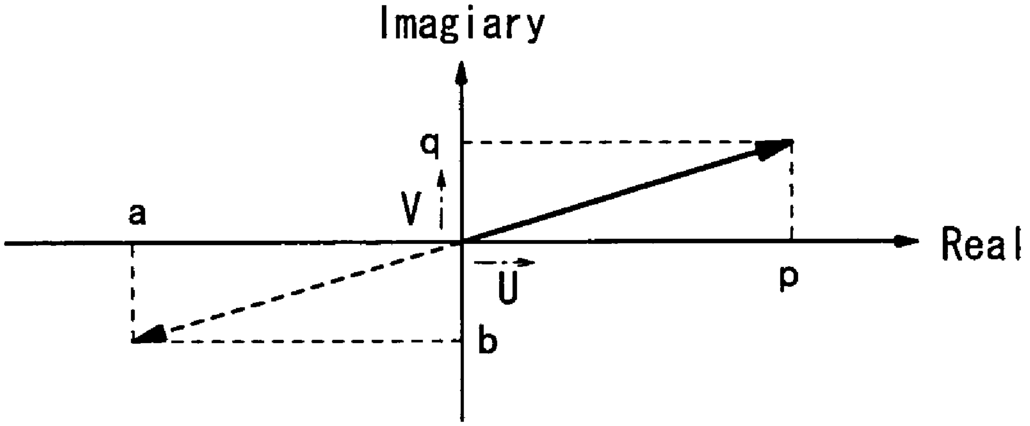
FIG. 4 is a diagram illustrative of a muffled-sound canceling process of the active vibratory noise control apparatus according to the embodiment of the present invention.

Muffled sounds of the engine represent vibratory noise having a narrow frequency band in synchronism with the rotation of the engine output shaft because the muffled sounds are produced due to gas combustion in the engine. All muffled sounds (waves) can be represented by the sum of mutually orthogonal cosine and sine waves having the control frequency (frequency) f of the muffled sounds. The muffled sounds can be expressed by a solid-line curve on a complex plane as shown in FIG. 4, i.e., expressed as ($p\cos 2\pi ft + iq\sin 2\pi ft$). Therefore, the muffled sounds can be expressed as a vector having two coefficients p, q by generating a reference cosine wave signal (Cs (=cos 2πft), 0) and a reference sine wave signal (0, Sn (=sin 2πft)) which are mutually orthogonal, as indicated by the dot-and-dash lines U, V.

The muffled sounds are thus expressed by the two coefficients p, q by making two mutually orthogonal reference wave signals. For canceling the muffled sounds which are vibratory noise, canceling vibratory noise having coefficients expressed by a (=−1×p), b=(−1×q), as indicated by the broken lines in FIG. 4 may be generated.

Figure 5:
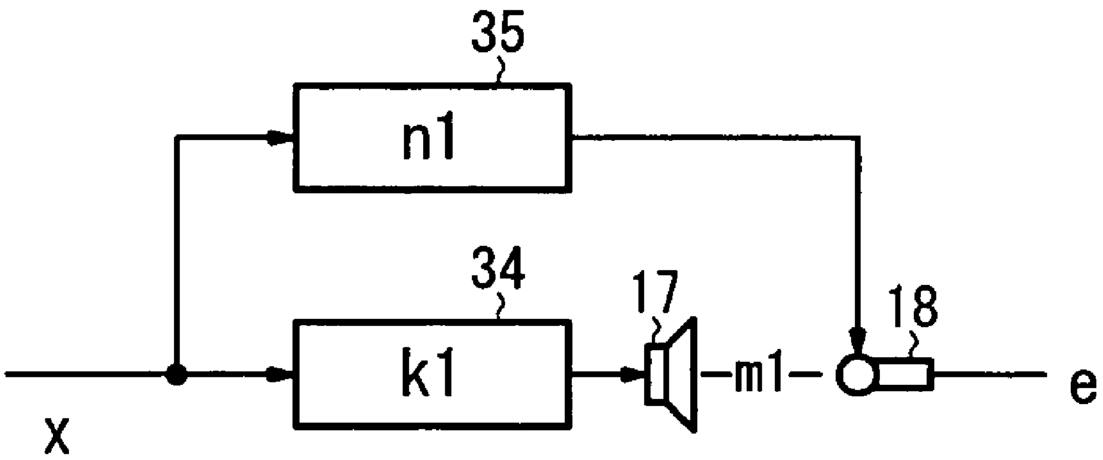
FIG. 5 is a block diagram of an arrangement for performing the muffled-sound canceling process of the active vibratory noise control apparatus according to the embodiment of the present invention.

The arrangement shown in FIG. 1 may be schematically represented as shown in FIG. 5. In FIG. 5, an input reference signal x having the control frequency based on the signal output from the frequency detecting circuit 11 is transmitted to the speaker 17 through a controller 34 having signal transfer characteristics k1 up to the speaker 17. Canceling vibratory noise output from the speaker 17 is transmitted through the passenger compartment having signal transfer characteristics m1, which is to be controlled at the frequency of the reference signal x, to the microphone 18. The reference signal x is also transmitted through an unknown system 35 such as a vehicle body having signal transfer characteristics n1 to the microphone 18, which produces an error signal e.

The signal transfer characteristics k1 of the controller 34 for producing the canceling vibratory noise is expressed by:

$$k1 = -n1/m1,$$

and the error signal e produced by the microphone 18 is expressed by:

$$e = n1\cdot x + k1\cdot m1\cdot x$$

The gradient Δ of a mean square error of the error signal e is expressed by the following equation (1):

$$\begin{aligned} \Delta &= \frac{\partial(e^2)}{\partial k1} \\ &= 2\cdot e\cdot\frac{\partial e}{\partial k1} \\ &= 2\cdot e\cdot m1\cdot x \end{aligned} \tag{1}$$

Figure 6:
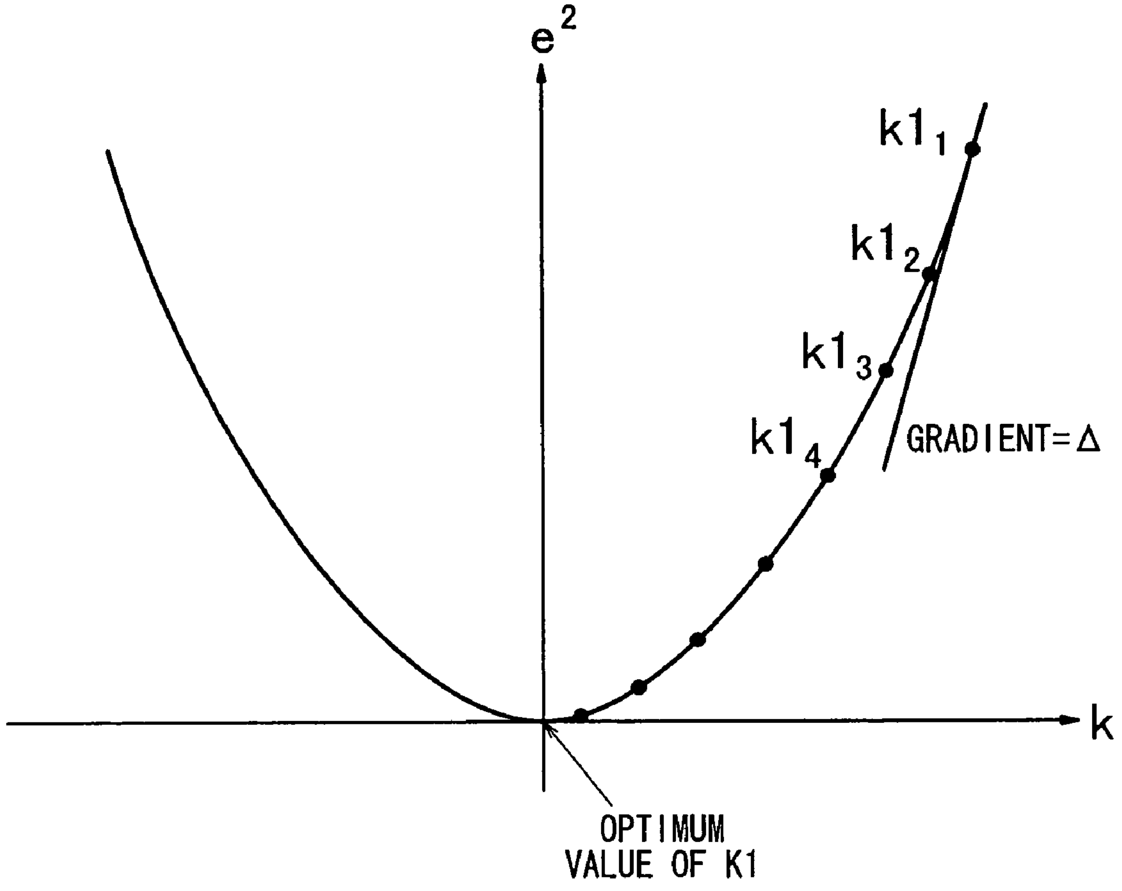
FIG. 6 is a diagram showing the relationship between signal transfer characteristics and an error signal for the muffled-sound canceling process of the active vibratory noise control apparatus according to the embodiment of the present invention.

Therefore, the gradient Δ of the mean square error of the error signal e which is produced under adaptive control is represented as shown in FIG. 6. In order to obtain an optimum value of the signal transfer characteristics k1 where the square error ($e^2$) is minimum, the equation (2), shown below, is repeatedly calculated. In the equation (2), n is an integer of 0 or more and represents the count of sampling pulses (timing signal count), as described above, for sampling the reference cosine wave for A/D conversion and sampling the reference sine wave for A/D conversion, which is also representative of the number of adaptive calculations that is incremented each time the filter coefficients are updated, and μ represents a step-size parameter. The equation (2) is an adaptive updating formula using LMS algorithm calculations, and serves to cancel vibratory noise according to an adaptive processing sequence.

$$k1_{n+1}=k1_n-\mu\cdot e_n\cdot m1\cdot x_n \qquad (2)$$

Specifically, in the active vibratory noise control apparatus 10, the signal transfer characteristics k1 is expressed as a signal a (=coefficient a) and a signal b (=coefficient b) which are mutually orthogonal.

The first and second reference signals $r_x(f,n)$, $r_y(f,n)$ will be described below with reference to FIGS. 7A through 7D.

In FIGS. 7A through 7D, when instantaneous values of the reference cosine wave signal (hereinafter also referred to as reference wave cos) and the reference sine wave signal (hereinafter also referred to as reference wave sin), which are reference wave signals, are directly output respectively as the signals Cs, Sn from the speaker 17, the reference waves cos, sin are transmitted to the microphone 18 according to the signal transfer characteristics from the speaker 17 to the microphone 18 which serves as an evaluating point. The process of how the reference waves cos, sin are changed when they reach the microphone 18 will be described below.

The signal transfer characteristics of the passenger compartment from the speaker 17 to the microphone 18 is divided into gain (instantaneous value change) and phase characteristics (phase lag).

The signal transfer characteristics from the speaker 17 to the microphone 18 are such that when the reference wave signals reach the microphone 18, the instantaneous value of these reference wave signals is multiplied by the gain α and the phase thereof is delayed ϕ degrees. The reference wave signals as they have reached the microphone 18 are represented respectively by New_Cs, New_Sn.

Only a phase lag (ϕ) with respect to a reference wave signal having a certain control frequency will be taken into account. The phase lag (ϕ) corresponds to a rotation of the reference wave signal (vector) on a complex plane about the origin by ϕ. Therefore, taking into account the phase lag (ϕ) only, a linear transformation matrix $P'_{lm}(\phi)$ for rotating the vector by the phase lag (ϕ) is expressed by the following equation (3):

$$P'_{1m}(\phi)=\begin{pmatrix}\cos\phi & i\sin\phi\\ i\sin\phi & \cos\phi\end{pmatrix} \qquad (3)$$

where $P'_{lm}(\phi)$ is a transformation formula for signal transfer characteristics when only the phase lag (ϕ) is taken into consideration, l is the number of speakers (the number of vibratory noise canceling signals that are output), and m is the number of microphones (the number of error signals that are input). If the number of speakers is 2 and the number of microphones is 2, then transformation matrixes $P'_{11}$, $P'_{12}$, $P'_{21}$, $P'_{22}$ are present in each signal transmission path.

A transformation formula $P_{lm}(\phi)$ for signal transfer characteristics when the gain α is also taken into account is expressed by the following equation (4):

$$P_{1m}(\phi)=\alpha\begin{pmatrix}\cos\phi & i\sin\phi\\ i\sin\phi & \cos\phi\end{pmatrix} \qquad (4)$$

The transformation formula $P_{lm}(\phi)$ can also easily be understood from the above equation (4).

Figure 7A:
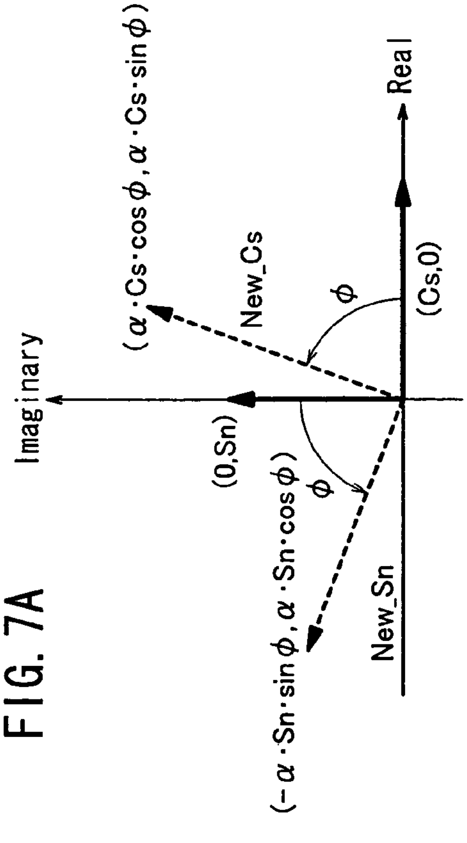
FIGS. 7A through 7D are diagrams illustrative of the manner in which muffled-sound canceling sounds are generated by the active vibratory noise control apparatus according to the embodiment of the present invention.

When instantaneous values of the reference cosine wave signal and the reference sine wave signal are represented by the signals Cs, Sn indicated by the solid lines in FIG. 7A, also taking into account the gain α in the signal transfer characteristics, the broken lines in FIG. 7A represent the signals New_Cs, New_Sn which the signals Cs, Sn are turned into when they reach the microphone 18 from the speaker 17 through the passenger compartment having the signal transfer characteristics having the gain α and the phase lag (ϕ).

That is, the reference cosine wave signal Cs and the reference sine wave signal Sn are turned respectively into the signals New_Cs, New_Sn by being multiplied by the gain α and rotated by the phase lag (ϕ) when they reach the microphone 18.

The signals New_Cs, New_Sn are expressed respectively by the following equations (5), (6):

$$\text{New\_Cs};\begin{pmatrix}Csr\\ Csi\end{pmatrix}=\alpha\begin{pmatrix}\cos\phi & i\sin\phi\\ i\sin\phi & \cos\phi\end{pmatrix}\begin{pmatrix}Cs\\ 0\end{pmatrix}=\begin{pmatrix}\alpha\cdot Cs\cdot\cos\phi\\ i\alpha\cdot Cs\cdot\sin\phi\end{pmatrix} \qquad (5)$$

$$\text{New\_Sn};\begin{pmatrix}Snr\\ Sni\end{pmatrix}=\alpha\begin{pmatrix}\cos\phi & i\sin\phi\\ i\sin\phi & \cos\phi\end{pmatrix}\begin{pmatrix}0\\ iSn\end{pmatrix}=\begin{pmatrix}-\alpha\cdot Sn\cdot\sin\phi\\ i\alpha\cdot Sn\cdot\cos\phi\end{pmatrix} \qquad (6)$$

If the signals New_Cs, New_Sn are represented as vectors, then they are expressed according to the equations (7) shown below, as shown in FIG. 7A.

$$\left.\begin{aligned}\text{New\_Cs}&=(\alpha\cdot Cs\cdot\cos\phi,\ \ i\alpha\cdot Cs\cdot\sin\phi)\\ \text{New\_Sn}&=(-\alpha\cdot Sn\cdot\sin\phi,\ \ i\alpha\cdot Sn\cdot\cos\phi)\end{aligned}\right\} \qquad (7)$$

Based on the fact that vibratory noise including muffled sounds are represented by a combination of the cosine wave signal and the sine wave signal, the active vibratory noise control apparatus 10 cancels the vibratory noise including the muffled sounds by sequentially updating the coefficient a on the real axis of a complex plane and the coefficient b on the imaginary axis of the complex plane as shown in FIG. 4 according to the LMS algorithms in order to minimize the error signal e at the position of the microphone 18. The coefficient a on the real axis (see FIG. 4) is sequentially updated based on the signal on the real axis at the position of the microphone 18, and the coefficient b on the imaginary axis (see FIG. 4) is sequentially updated based on the signal on the imaginary axis at the position of the microphone 18, thereby suppressing vibratory noise. Therefore, it is necessary to determine the signal on the real axis and the signal on the imaginary axis from the signals New_Cs, New_Sn.

Now, a process of determining the coefficient a on the real axis and the coefficient b on the imaginary axis from the signals New_Cs, New_Sn will be described below.

Figure 7B:
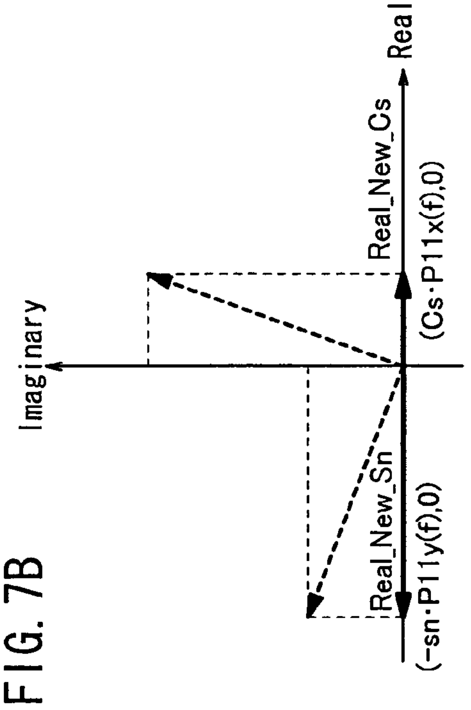
Figure 7C:
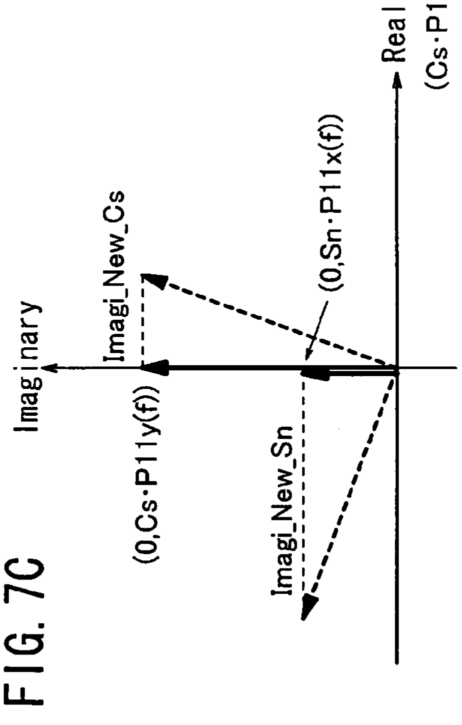

The magnitudes of real components included in the signals New_Cs, New_Sn are obtained by projecting those signals onto the real axis. Their values are represented by Real_New_Cs (also referred to as Real_Cs) and Real_New_Sn (also referred to as Real_Sn), respectively, as shown in FIG. 7B. The magnitudes of imaginary components included in the signals New_Cs, New_Sn are obtained by projecting those signals onto the imaginary axis. Their values are represented by Imagi_New_Cs (also referred to as Imagi_Cs) and Imagi_New_Sn (also referred to as Imagi_Sn), respectively, as shown in FIG. 7C.

Figure 7D:
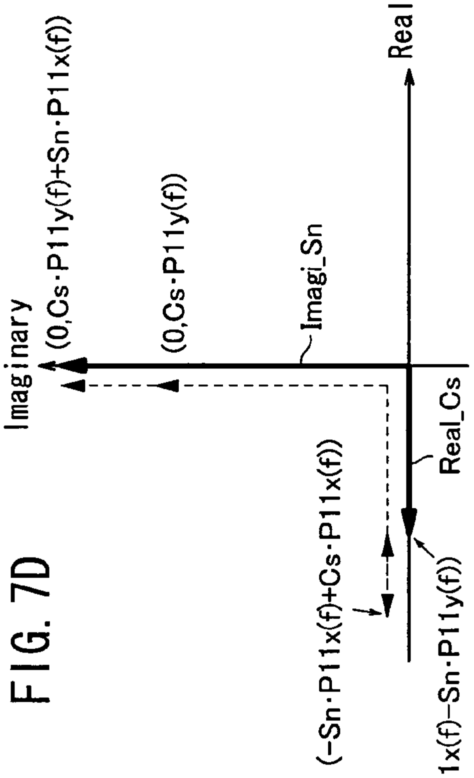
Figure 17:
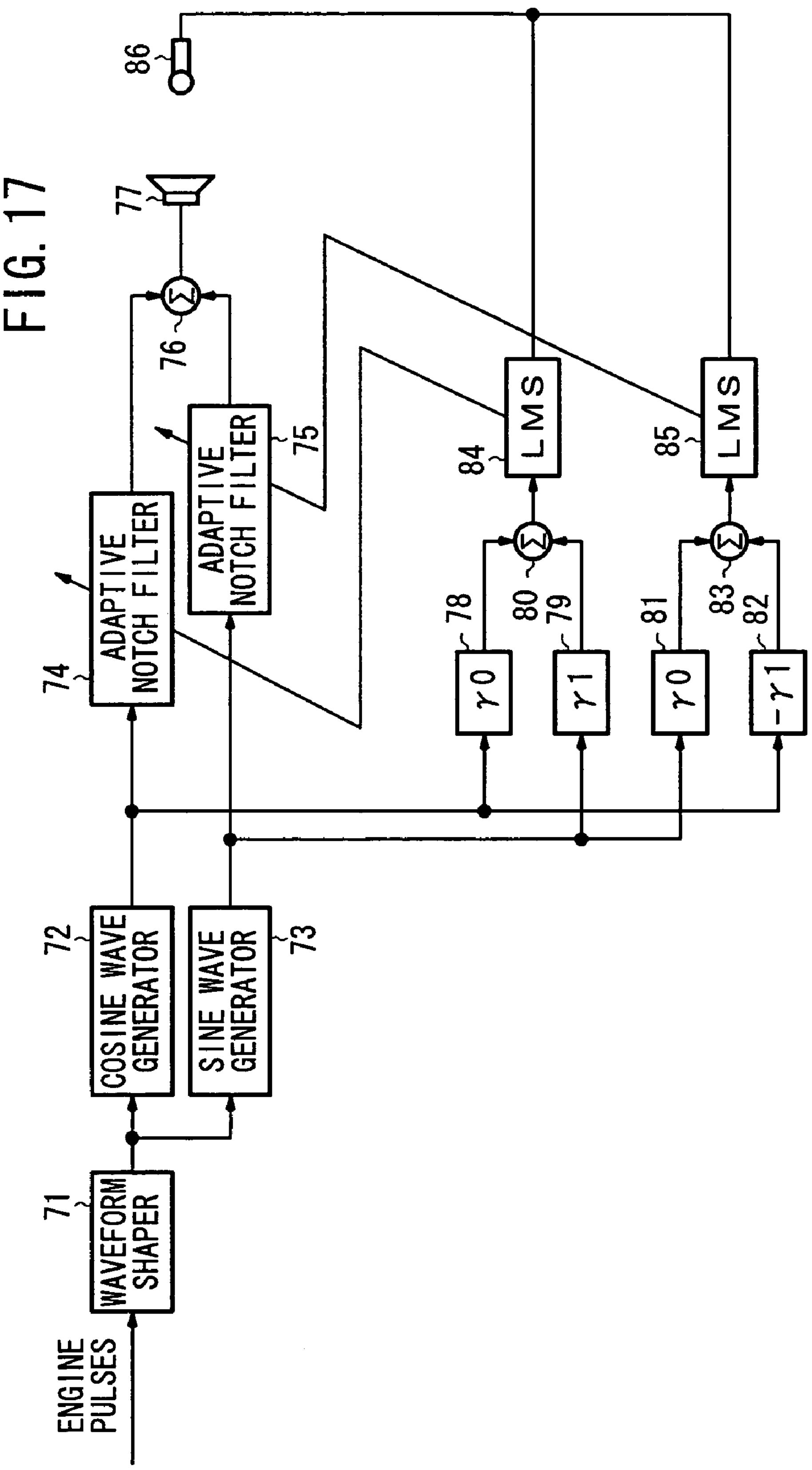
FIG. 17 is a block diagram of a conventional active vibratory noise control apparatus which employs adaptive notch filters.

When the reference cosine wave signal Cs and the reference sine wave signal Sn are multiplied by the gain α and rotated by the phase lag (ϕ) according to the signal transfer characteristics of the passenger compartment from the speaker 17 to the microphone 18 in FIGS. 17B and 17C, their real components and imaginary components are indicated by the broken lines in FIG. 7D. These real components and imaginary components are combined into Real_Cs, Imagi_Sn, respectively, as indicated by the solid lines in FIG. 7D.

The signals on the real and imaginary axes are determined by calculations as follows:

The signals produced on the real and imaginary axes by projecting the signal New_Cs onto the real and imaginary axes are represented by Real_New_Cs (vector RNCs) and Imagi_New_Cs (vector INCs), respectively. The signals produced on the real and imaginary axes by projecting the signal New_Sn onto the real and imaginary axes are represented by Real_New_Sn (vector RNSn) and Imagi_New_Sn (vector INSn), respectively. The signal Real_Cs on the real axis is represented by (vector RCs), the signal Imagi_Sn on the imaginary axis by (vector ISn), the signal New_Cs by (vector NSn), the signal Cs by (vector Cs), and the signal Sn by (vector Sn). In the equations shown below, a vector is indicated by an arrow as a hat.

The vector RCs is the sum of the vector RNCs and the vector RNSn, and the vector RNCs and the vector RNSn are produced by projecting the vector NCs or the vector NSn onto the vector Cs. Therefore, the vector RNCs and the vector RNSn are expressed by the following equations (8):

$$\left.\begin{aligned} \overrightarrow{RNCs} &= \frac{\overrightarrow{Cs}\times\overrightarrow{NCs}}{\overrightarrow{Cs}\times\overrightarrow{Cs}}\cdot\overrightarrow{Cs} \\ &= \frac{\alpha\cdot Cs^2\cdot\cos\phi}{Cs^2}\cdot\overrightarrow{Cs} = \alpha\cdot\cos\phi(Cs,\,0) \\ &= (\alpha\cdot Cs\cdot\cos\phi,\,0) \\ \overrightarrow{RNSn} &= \frac{\overrightarrow{Cs}\times\overrightarrow{NSn}}{\overrightarrow{Cs}\times\overrightarrow{Cs}}\cdot\overrightarrow{Cs} = \frac{-\alpha\cdot Cs\cdot Sn\cdot\sin\phi}{Cs^2}\cdot\overrightarrow{Cs} \\ &= -\frac{-\alpha\cdot Sn}{Cs}\cdot\sin\phi(Cs,\,0) = (-\alpha\cdot Sn\cdot\sin\phi,\,0) \end{aligned}\right\} \quad (8)$$

Therefore, the vector RCs is expressed by the following equation (9):

$$\begin{aligned} \overrightarrow{RCs} &= (\alpha\cdot Cs\cdot\cos\phi - \alpha\cdot Sn\cdot\sin\phi,\,0) \\ &= \alpha(Cs\cdot\cos\phi - Sn\cdot\sin\phi,\,0) \end{aligned} \quad (9)$$

Since the vector ISn is the sum of the vector INCs and the vector INSn, and the vector INCs and the vector INSn are produced by projecting the vector NCs or the vector NSn onto the vector Sn, the vector INCs and the vector INSn are expressed by the following equations (10):

$$\left.\begin{aligned} \overrightarrow{INCs} &= \frac{\overrightarrow{Sn}\times\overrightarrow{NCs}}{\overrightarrow{Sn}\times\overrightarrow{Sn}}\cdot\overrightarrow{Sn} = \frac{-\alpha\cdot Cs\cdot Sn\cdot\sin\phi}{-Sn^2}\cdot\overrightarrow{Sn} \\ &= \frac{\alpha\cdot Cs}{Sn}\cdot\sin\phi(0,\,i\mathrm{Sn}) = (0,\,i\alpha\cdot Cs\cdot\sin\phi) \\ \overrightarrow{INSn} &= \frac{\overrightarrow{Sn}\times\overrightarrow{NSn}}{\overrightarrow{Sn}\times\overrightarrow{Sn}}\cdot\overrightarrow{Sn} = \frac{-\alpha\cdot Sn^2\cdot\cos\phi}{-Sn^2}\cdot\overrightarrow{Sn} \\ &= \alpha\cdot\cos\phi(0,\,i\mathrm{Sn}) = (0,\,i\alpha\cdot Sn\cdot\cos\phi) \end{aligned}\right\} \quad (10)$$

Therefore, the vector ISn is expressed by the following equation (11):

$$\begin{aligned} \overrightarrow{ISn} &= (0,\,i[\alpha\cdot Cs\cdot\sin\phi + \alpha\cdot Sn\cdot\cos\phi]) \\ &= i\alpha(0,\,Cs\cdot\sin\phi + Sn\cdot\cos\phi) \end{aligned} \quad (11)$$

The signal transfer characteristics are functions of the frequency of the output sound from the speaker 17. The signal transfer characteristics are thus expressed using complex numbers, as follows:

$$P_{lm}(f)=P_{lmx}(f)+iP_{lmy}(f)$$

$$P_{lmx}(f)=\alpha(f)\cdot\cos\phi(f)$$

$$P_{lmy}(f)=\alpha(f)\cdot\sin\phi(f)$$

If the full control frequency range of the reference wave signals is taken into consideration, then the vector RCs and the vector ISn are expressed by the equations (12) shown below (see FIG. 7D). These vectors represent the real and imaginary components of the finally combined signal.

$$\overrightarrow{RCs}=(Cs\cdot P_{lmx}(f)-Sn\cdot P_{lmy}(f),\,0)$$

$$\overrightarrow{ISn}=(0\,,\,i[Cs\cdot P_{lmy}(f)+Sn\cdot P_{lmx}(f)]) \quad (12)$$

From the above equations, the first reference signal $r_x(f)$ which is used to update the filter coefficients (corresponding to the coefficient a in FIG. 4) of the first adaptive notch filter 14 is expressed as follows:

$$r_x(f)=Cs\cdot P_{lmx}(f)-Sn\cdot P_{lmy}(f)$$

The second reference signal $r_y(f)$ which is used to update the filter coefficients (corresponding to the coefficient b in FIG. 4) of the second adaptive notch filter 15 is expressed as follows:

$$r_y(f)=Cs\cdot P_{lmy}(f)+Sn\cdot P_{lmx}(f)$$

Inasmuch as the signal Cs is an instantaneous value of the reference cosine wave signal and the signal Sn is an instantaneous value of the reference sine wave signal, the reference signals are given as indicated by the equations (13) shown below.

$$\left.\begin{aligned} r_x(f) &= P_{1mx}(f)\cdot\cos2\pi ft - P_{1my}(f)\cdot\sin2\pi ft \\ r_y(f) &= P_{1my}(f)\cdot cos2\pi\, ft + P_{1mx}(f)\cdot\sin2\pi ft \end{aligned}\right\} \quad (13)$$

The reference signals $r_x(f)$, $r_y(f)$ represented by the equations (13) are expressed using n referred to above, as follows: The reference signals $r_x(f,n)$, $r_y(f,n)$ are given by the following equations (14), from $P_{lm}(f)=\alpha(f)\cdot\cos\phi(f)$, $P_{lm}(f)=\alpha(f)\cdot\sin\phi(f)$ and the addition theorems of the trigonometric functions:

$$\begin{aligned} r_x(f,n) &= P_{1mx}(f)\cdot\cos2\pi(f,n) - P_{1my}(f)\cdot\sin2\pi(f,n) \\ &= \alpha(f)[\cos(\phi(f))\cdot\cos2\pi(f,n) - \sin(\phi(f))\cdot\sin2\pi(f,n)] \\ &= \alpha(f)[\cos\{2\pi(f,n)+\phi(f)\}] \\ r_y(f,n) &= P_{1my}(f)\cdot\cos2\pi(f,n) + P_{1mx}(f)\cdot\sin2\pi(f,n) \\ &= \alpha(f)[\sin(\phi(f))\cdot\cos2\pi(f,n) + \cos(\phi(f))\cdot\sin2\pi(f,n)] \\ &= \alpha(f)[\sin\{2\pi(f,n)+\phi(f)\}] \end{aligned} \quad (14)$$

where $\alpha(f)$ represents a gain, which may be a coefficient with respect to cos $\{2\pi(f,n)+\phi(f)\}$, sin $\{2\pi(f,n)+\phi(f)\}$. If signals produced by dividing the first and second reference signals $r_x(f,n)$, $r_y(f,n)$ by the gain $\alpha(f)$ are referred to as a first basic reference signal $r_a(f,n)$ and a second basic reference signal $r_b(f,n)$, respectively, then the first basic reference signal $r_a$(f, n) and the second basic reference signal $r_b(f,n)$ are expressed by the following equations (15-1), (15-2):

$$r_a(f,n) = r_x(f,n)/\alpha(f) = \cos\{2\pi(f,n)+\phi(f)\} \quad (15\text{-}1)$$

$$r_b(f,n) = r_y(f,n)/\alpha(f) = \sin\{2\pi(f,n)+\phi(f)\} \quad (15\text{-}2)$$

Figure 10:
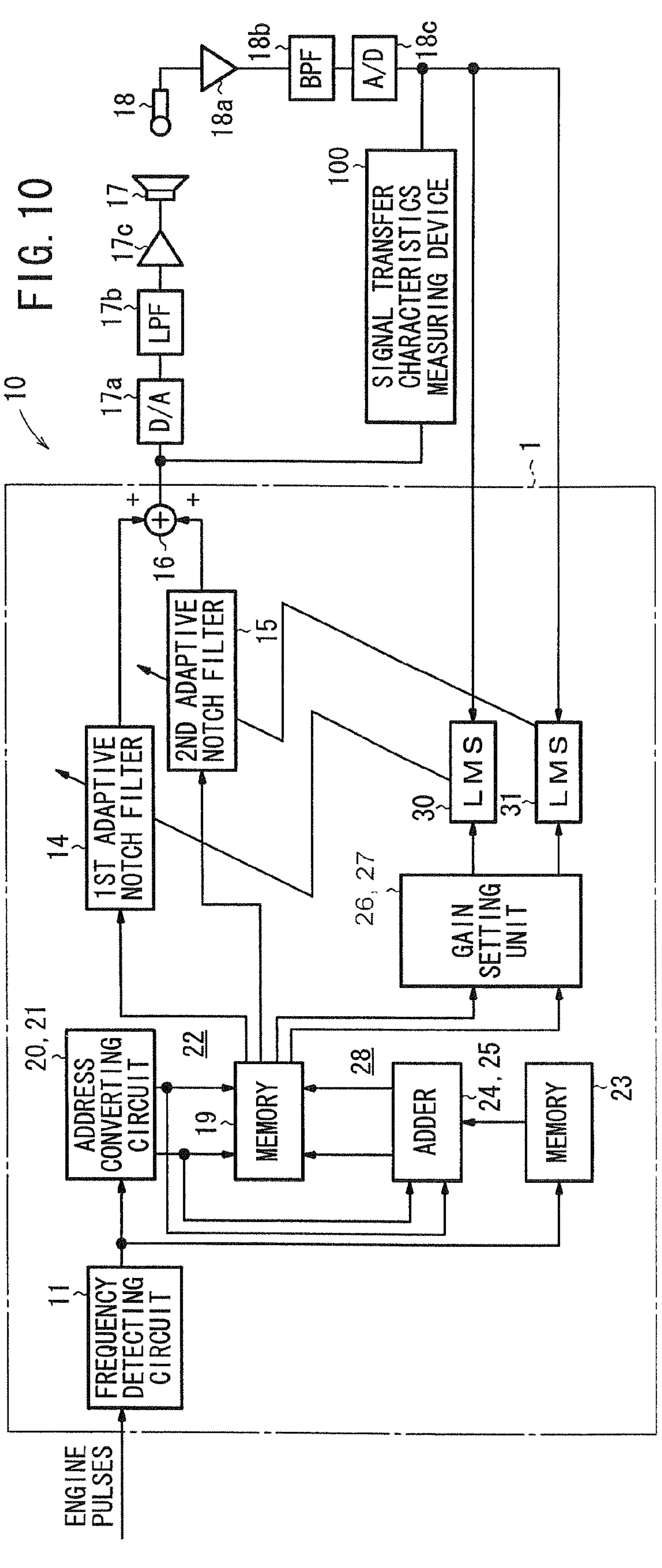
FIG. 10 is a block diagram of a system for measuring signal transfer characteristics of the active vibratory noise control apparatus according to the embodiment of the present invention.

Therefore, it can be seen from the equation (15-1) that $r_a(f,n)$ represents a cosine wave signal which lags in phase by $\phi n(f)$ behind the reference cosine wave signal ($\cos 2\pi(f,n)$), and from the equation (15-2) that $r_b(f,n)$ represents a sine wave signal which lags in phase by $\phi n(f)$ behind the reference sine wave signal ($\sin 2\pi(f,n)$). As shown in FIG. 10 to be described later, phase characteristics (phase lag) $\phi n(f)$ of respective control frequencies may be determined in advance, and the memory 23 may be provided which stores in advance corrective values based on $\phi n(f)$ in association with the control frequencies of the reference wave signals, as address shift values for the addresses for reading the reference wave signals from the memory 19.

As a result, a control frequency is referred to, and an address shift value depending on the control frequency is read from the memory 23. The address shift value and the address data output from the first and second address converting circuits 20, 21 are added by the adders 24, 25 into sum values to designate addresses of the memory 19. The first basic reference signal $r_a(f,n)$ and the second basic reference signal $r_b(f,n)$, which represent the waveform data read from the designated addresses of the memory 19, are multiplied by the gain $\alpha(f)$ set in the gain setting units 26, 27, producing the first and second reference signals ($r_x(f,n)$, $r_y(f,n)$). Thus, the active vibratory noise control apparatus 10 is of the arrangement shown in FIG. 1.

From FIG. 6, equations for updating the filter coefficients are provided as $a_1(n+1)=a_1(n)-\mu\cdot e_m(n)\cdot r_x(f,n)$ and $b_1(n+1)=b_1(n)-\mu\cdot e_m(n)\cdot r_y(f,n)$ by replacing kln with $a_1(n)$, $b_1(n)$, k1 with a and b, and m1·x with r(f,n) in the equation (2). Based on the reference signal $r_x(f,n)$, the former equation is given as the equation (16-1) shown below, and based on the reference signal $r_y(f,n)$, the latter as the equation (16-2) shown below.

$$\begin{aligned} a_1(n+1) &= a_1(n) - \mu\cdot e_m(n)\cdot\alpha(f)[\cos(\phi(f))\cdot\cos 2\pi(f,n) - \sin(\phi(f))\cdot\sin 2\pi(f,n)] \\ &\quad a_1(n) - \mu\cdot e_m(n)\cdot\alpha(f)[\cos\{2\pi(f,n)+\phi(f)\}] \\ &\quad a_1(n) - \mu\cdot e_m(n)\cdot\alpha(f)\cdot r_a(f,n) \\ &\quad a_1(n) - \mu'(f)\cdot e_m(n)\cdot r_a(f,n) \end{aligned} \quad (16\text{-}1)$$

$$\begin{aligned} b_1(n+1) &= b_1(n) - \mu\cdot e_m(n)\cdot\alpha(f)[(\sin(\phi(f))\cdot\cos 2\pi(f,n) + \cos(\phi(f))\cdot\sin 2\pi(f,n)] \\ &\quad b_1(n) - \mu\cdot e_m(n)\cdot\alpha(f)[\sin\{2\pi(f,n)+\phi(f)\}] \\ &\quad b_1(n) - \mu\cdot e_m(n)\cdot\alpha(f)\cdot r_b(f,n) \\ &\quad b_1(n) - \mu'(f)\cdot e_m(n)\cdot r_b(f,n) \end{aligned} \quad (16\text{-}2)$$

From the above equation (14), $\alpha(f)$ which reflects the gain of the signal transfer characteristics in the reference signal $r_x(f,n)$ and the reference signal $r_y(f,n)$ can be a coefficient for each frequency, and is synonymous with changing from a constant step size parameter $\mu$ to a step size parameter $\mu'$ at each control frequency as indicated by the equations (16-1), (16-2). This also means that the reference signal $r_x(f,n)$ and the reference signal $r_y(f,n)$ may accurately reflect only the phase lag ($\phi$) of the signal transfer characteristics, and that $\alpha(f)$ which reflects the gain of the signal transfer characteristics can be substituted for an adjusting element at each control frequency.

In the active vibratory noise control apparatus 10, as described above, the frequency of the reference cosine wave signal, the frequency of the reference sine wave signal, the frequency of the reference signal $r_x(f,n)$, and the frequency of the reference signal $r_y(f,n)$ change based on the rotational speed of the engine output shaft, and the notch frequencies of the first and second adaptive notch filters 14, 15 operate in the same manner as if they virtually change based on the rotational speed of the engine output shaft, canceling the vibratory noise including muffled sounds.

In the active vibratory noise control apparatus 10, furthermore, since the signal transfer characteristics is optimally modeled using the reference signal $r_x(f,n)$, and the reference signal $r_y(f,n)$, and the muffled sounds are canceled using the adaptive notch filters, the contours of constant square error curves become concentric circles, converging the cancellation of vibratory noise quickly.

The active vibratory noise control apparatus 10 as it is incorporated in a motor vehicle will be described below by way of specific example.

Figure 8:
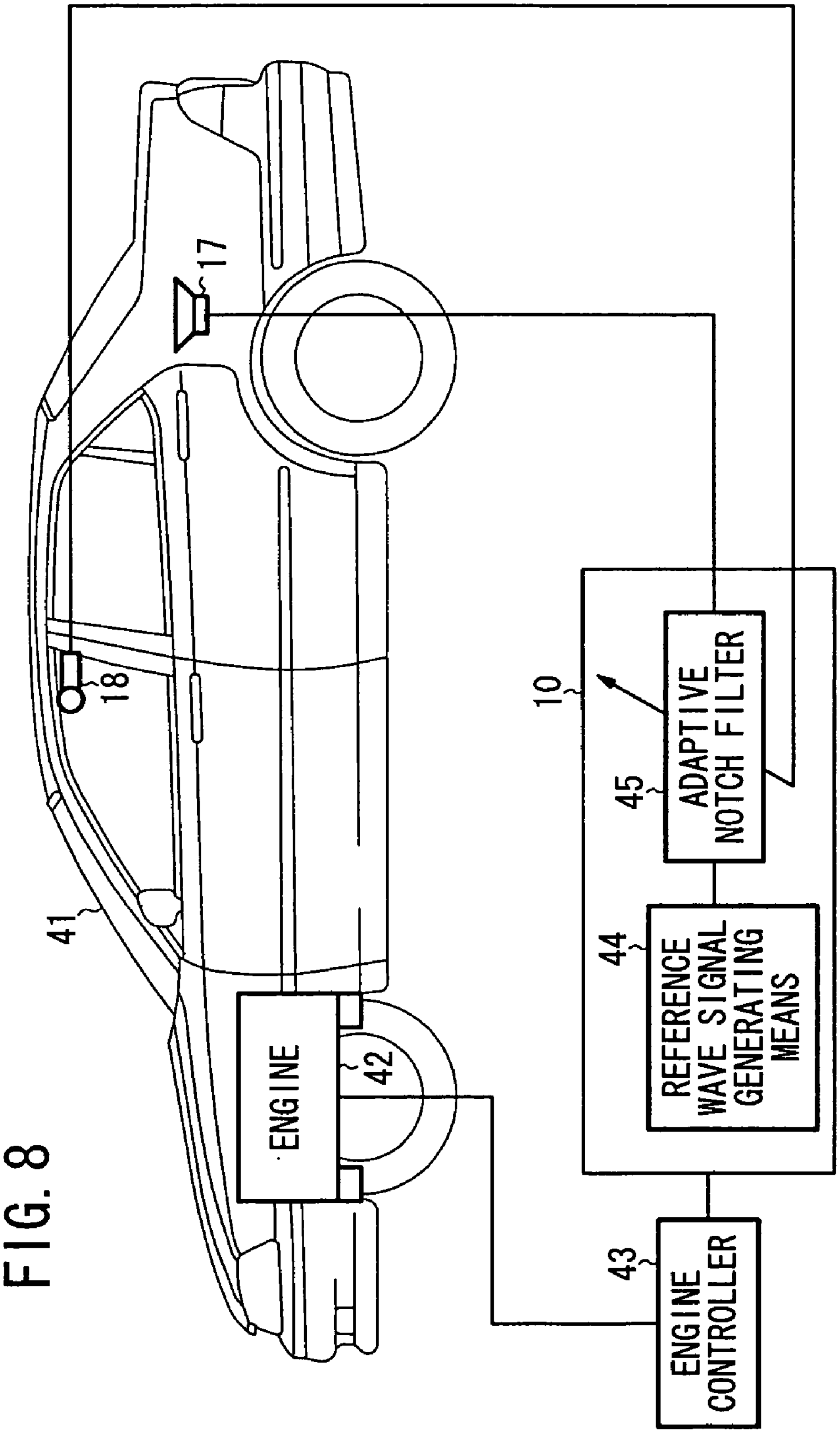
FIG. 8 is a block diagram showing a system in which the active vibratory noise control apparatus according to the embodiment of the present invention is incorporated in a motor vehicle.

FIG. 8 shows in block form a system in which the active vibratory noise control apparatus 10 with one microphone is incorporated in a motor vehicle for canceling the vibratory noise including muffled sounds in the passenger compartment of the vehicle.

In FIG. 8, the active vibratory noise control apparatus 10 has primary components which are functionally implemented by an inexpensive microcomputer. In FIG. 8, the reference wave signal generating means 22 and the reference signal generating circuit 28 shown in FIG. 1 are represented by a reference wave signal generating means 44, and the first adaptive notch filter 14, the second adaptive notch filter 15, and the LMS algorithm processors 30, 31 shown in FIG. 1 are represented by an adaptive notch filter 45. The D/A converter, the low-pass filter, the amplifier, the bandpass filter, and the A/D converter shown in FIG. 1 are omitted from illustration in FIG. 8, and also omitted from illustration in FIGS. 15 and 16 to be described later.

The speaker 17 is disposed in a given position behind the rear seats in a motor vehicle 41, and the microphone 18 is disposed on a central portion of the ceiling of the passenger compartment of the motor vehicle 41. The microphone 18 may alternatively be placed in the instrumental panel rather than on the ceiling of the passenger compartment.

Engine pulses output from an engine controller 43 which controls an engine 42 of the motor vehicle 41 are input to the active vibratory noise control apparatus 10 which coacts with the speaker 17 and the microphone 18. The adaptive notch filter 45 which is adaptively controlled to minimize an output signal from the microphone 18 applies an output signal to energize the speaker 17 to cancel vibratory noise in the passenger compartment of the motor vehicle 41. The process of canceling vibratory noise has already been described above with respect to the active vibratory noise control apparatus 10.

Measured values of the gain and phase lag in the signal transfer characteristics at various frequencies in the passenger compartment between the speaker 17 and the microphone 18 in the motor vehicle 41 are shown in FIGS. 9A and 9B. The measured values of the gain and the phase lag at the various frequencies are shown in the form of a table in FIG. 9C. In FIG. 9C, the gain is indicated in dB, and the phase lag ($\phi$) in an angle ($0°\leqq\phi\leqq 360°$).

In the description so far, the signal transfer characteristics are given as being present between the speaker 17 and the microphone 18 in the passenger compartment. Actually, as shown in FIG. 10, the signal transfer characteristics are measured by a signal transfer characteristics measuring device 100 comprising a Fourier transform device which is connected to the active vibratory noise control apparatus 10. Specifically, the signal transfer characteristics measuring device 100 measures the signal transfer characteristics based on a signal which is output from the microcomputer 1 to the speaker 17 and a signal which is input from the microphone 18 to the microcomputer 1.

Therefore, depending on the process of measuring the signal transfer characteristics, the signal transfer characteristics between the speaker 17 and the microphone 18 in the passenger compartment includes those characteristics which are caused by analog circuits inserted between the output and input of the microcomputer 1, e.g., the speaker 17, the microphone 18, the D/A converter 17*a*, the low-pass filter 17*b*, the amplifier 17*c*, the amplifier 18*a*, the bandpass filter 18*b*, and the A/D converter 18*c*.

Stated otherwise, depending on the process of measuring the signal transfer characteristics, the signal transfer characteristics between the speaker 17 and the microphone 18 in the passenger compartment become signal transfer characteristics from the outputs of the adaptive notch filters to the inputs of the LMS algorithm processors 30, 31 (=filter coefficient updating means).

Address shift values based on the phase lag $\phi$ at respective control frequencies according to measured values of the gain and the phase lag $\phi$ are shown in FIG. 9D in association with the respective control frequencies. The address shift values corresponding to the frequencies of the reference wave signals are stored in the memory 23. It is assumed that the memory 19 has 3600 addresses ranging from 0 to 3599 and stores waveform data of a sine wave signal. Since corrective values (address shift values) are determined by $\phi(f)\times N/3600$, and a phase lag of 0.1 degree corresponds to one address of the memory 19 in the embodiment, the memory 23 stores address shift values as shown in FIG. 9D for the respective phase lags shown in FIG. 9C.

In the embodiment of the present invention, muffled sounds of the engine are canceled in the motor vehicle 41 on which the 4-cycle 4-cylinder engine is mounted. The control frequency ranges from 40 Hz to 200 Hz as rotational secondary components corresponding to engine rotational speeds from 1200 rpm to 6000 rpm. In view of the possibility of malfunctioning of the microcomputer serving as the active vibratory noise control apparatus 10 (hereinafter also referred to as vibratory noise control microcomputer), the signal transfer characteristics are measured in a control frequency range from 30 Hz to 230 Hz, and address shift values are stored in the control frequency range from 30 Hz to 230 Hz, as shown in FIG. 9D.

If a frequency value outside of the control frequency range were determined as a result of reference wave signal frequency calculations, then the address shift values would not be read, and the microcomputer for vibratory noise control would run out of control. The corrective values are stored in the above wider control frequency range in order to prevent the microcomputer from running out of control. In the embodiment of the present invention, since an 8-bit microcomputer is used as the microcomputer 1 in the process of calculating the values shown in FIG. 9D from the values shown in FIG. 9C, the gain $\alpha$ used in the calculations is set to $\alpha=127$ when the measurement gain is 0 (dB).

Therefore, when the amplification degree is A, since the gain=20 logA, the gain is (gain/20)th power to A=10. If gain=−6, the gain $\alpha=127\times A=(-6/20)$th power to $127\times10=63.651$. The values of the gain $\alpha$ shown in FIG. 9E with respect to the gain characteristics shown in FIG. 9C are set in the gain setting units 26, 27.

The active vibratory noise control apparatus 10 incorporated in the motor vehicle 41 operates as follows: When the reference frequency f is 40 Hz, waveform data is read from every 40 addresses of the memory 19 to produce a reference sine wave signal, and waveform data is read from addresses of the memory 19 which are represented by the sum of the reference sine wave signal readout addresses and 900 addresses to produce a reference cosine wave signal. These reference sine and cosine wave signals are supplied respectively to the second and first adaptive notch filters 15, 14. Similarly, an address shift value 3488 is read from the memory 23. Waveform data is read as a second basic reference signal from addresses of the memory 19 that are 3488 shifted from the addresses from which the waveform data of the reference sine wave signal of 40 Hz were read, and waveform data is read as a first basic reference signal from addresses of the memory 19 that are 3488 shifted from the addresses from which the waveform data of the reference cosine wave signal of 40 Hz were read. These first and second basic reference signals are supplied to the LMS algorithm processors 31, 30, respectively.

The above process will be described in greater detail with reference to FIGS. 11A through 11C. The memory 19 stores instantaneous value data as waveform data at respective addresses (i=0, 40, 80, 120, . . . , 3599) so that the predetermined number=3600 (N=3600) of data represent instantaneous values of a sine wave over one period. The frequency detecting circuit 11 outputs a sampling pulse (timing signal) at a constant sampling interval 1/3600 (t=1/N), and also outputs a control frequency f=40 Hz, for example. Since the control frequency is 40 Hz, the first address converting circuit 20 successively outputs addresses i(n) at address intervals=40 (is=N×f×t) depending on the timing signal.

Figure 11A:
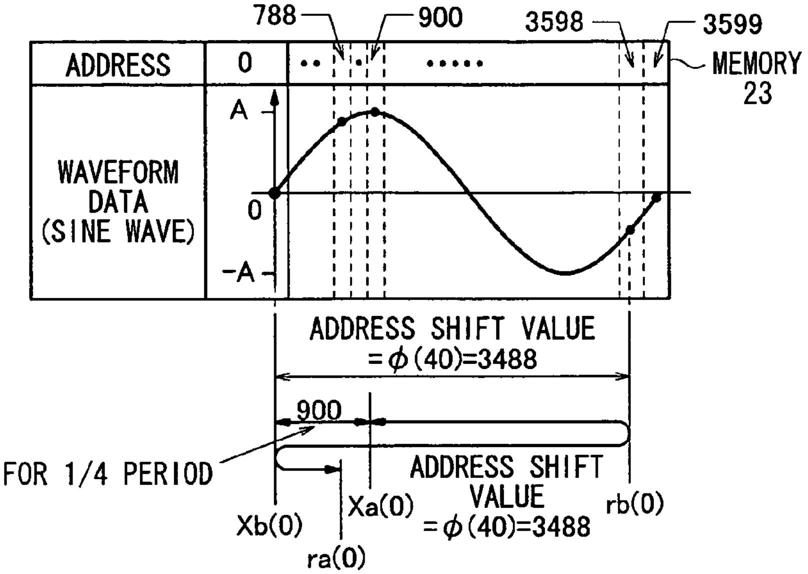
FIGS. 11A through 11C are diagrams showing address shift values in the system in which the active vibratory noise control apparatus according to the embodiment of the present invention is incorporated in the motor vehicle.
Figure 11B:
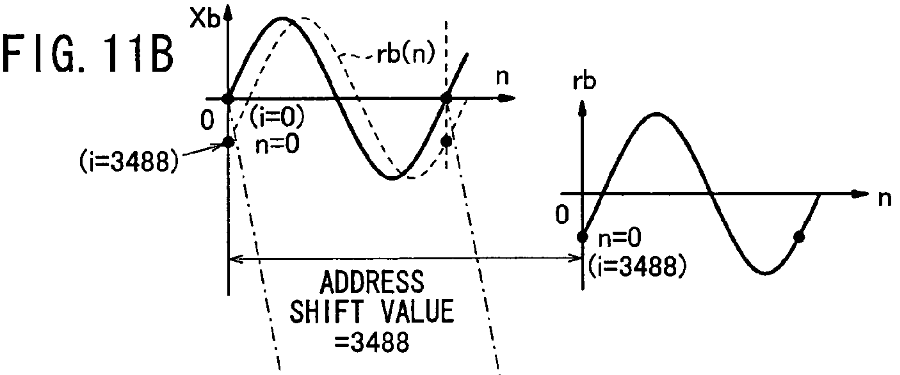

The reference wave signal generating means 22 successively reads waveform data corresponding to the addresses i(n)=0, 40, 80, 120, . . . , 3599, 0, . . . at respective intervals of 1/3600 sec., generating a reference sine wave signal Xb(n) of 40 Hz, which is output to the second adaptive notch filter 15 (see FIG. 11A).

From the memory 23, an address shift value (corrective value) S(f)=3488 corresponding to the control frequency f=40 Hz is read and applied to the adder 25. The adder 25 outputs addresses ib(n) which are the sums of the readout addresses i(n) of the reference sine wave signal Xb(n) output from the first address converting circuit 20 and the address shift value, according to the equation (15-2). Specifically, addresses that are produced by shifting the readout addresses i(n) of the reference sine wave signal Xb(n) by the address shift value S(f)=3488 corresponding to the phase lag ($\phi$) are designated as readout addresses ib(n) of the second basic reference signal.

Therefore, ib(n)=i(n)+S(f)=i(n)+3488

When i(n)>3599 (=N−1), ib(n)=i(n)+S(f)−3600

Therefore, the reference signal generating circuit 28 successively reads waveform data from the addresses of the memory 19 which are produced by shifting the readout addresses of the reference sine wave signal by the address shift value depending on the control frequency, at respective sampling pulses generated by the frequency detecting circuit 11, thereby generating a second basic reference signal rb(n).

Based on the second basic reference signal rb(n), the gain setting unit 27 generates and outputs a second reference signal $r_y(n)$. Specifically, the reference signal generating circuit 28 successively reads waveform data corresponding to the addresses ib(n)=3488, 3528, 3568, 8, . . . , 3448, 3488, . . . at respective intervals of 1/3600 sec., thereby generating the second basic reference signal rb(n) of 40 Hz, which is output through the gain setting unit 27 as the second reference signal to the LMS algorithm processor 31 (see FIG. 11B).

The second address converting circuit 21 outputs addresses which are produced by shifting the readout addresses of the reference sine wave signal that are output from the first address converting circuit 20, by a quarter of the period (N/4=900), as readout addresses i'(n).

Figure 11C:
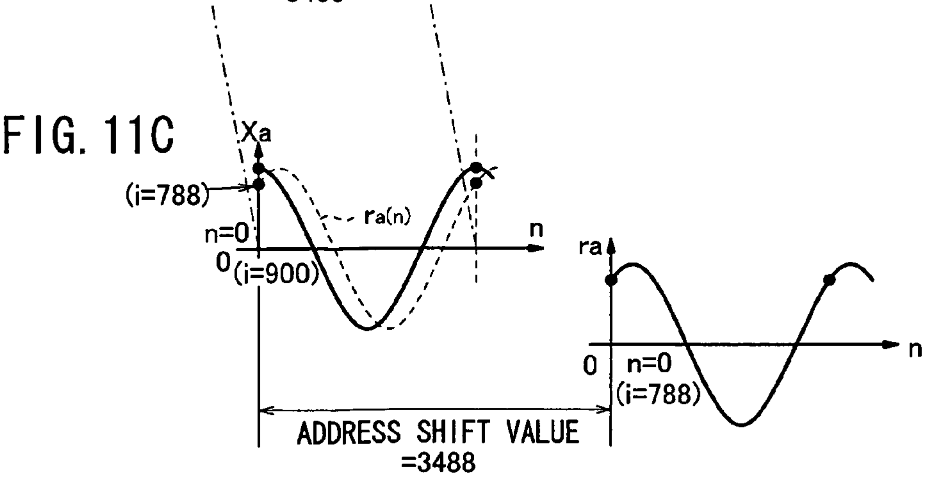

The reference wave signal generating means 22 successively reads waveform data corresponding to the addresses i'(n)=900, 980, 1020, . . . , 860, 900 . . at respective intervals of 1/3600 sec., generating a reference cosine wave signal Xa(n) of 40 Hz, which is output to the first adaptive notch filter 14 (see FIG. 11C).

From the memory 23, an address shift value (corrective value) S(f)=3488 corresponding to the control frequency f=40 Hz is read and applied to the adder 24. The adder 24 outputs addresses ia(n) which are the sums of the readout addresses i'(n) of the reference cosine wave signal Xa(n) output from the second address converting circuit 21 and the address shift value S(f)=3488 read from the memory 23, according to the equation (15-1). Specifically, addresses that are produced by shifting the readout addresses i'(n) of the reference cosine wave signal Xa(n) by the address shift value S(f)=3488 corresponding to the phase lag (ϕ) are designated as readout addresses ia(n) of the first basic reference signal.

Therefore, ia(n)=i'(n)+S(f)=i(n)+3488

When i(n)>3599 (=N−1), ib(n)=i'(n)+S(f)−3600

Therefore, the reference signal generating circuit 28 successively reads waveform data from the addresses of the memory 19 which are produced by shifting the readout addresses of the reference cosine wave signal by the address shift value depending on the control frequency, at respective sampling pulses generated by the frequency detecting circuit 11, thereby generating a first basic reference signal ra(n). Based on the first basic reference signal ra(n), the gain setting unit 26 generates and outputs a first reference signal $r_x(n)$. Specifically, the reference signal generating circuit 28 successively reads waveform data corresponding to the addresses ib(n)=788, 828, 868, 908, . . . , 748, 788, . . . at respective intervals of 1/3600 sec., thereby generating the first basic reference signal ra(n) of 40 Hz, which is output through the gain setting unit 26 as the first reference signal to the LMS algorithm processor 30 (see FIG. 11C).

Figure 12A:
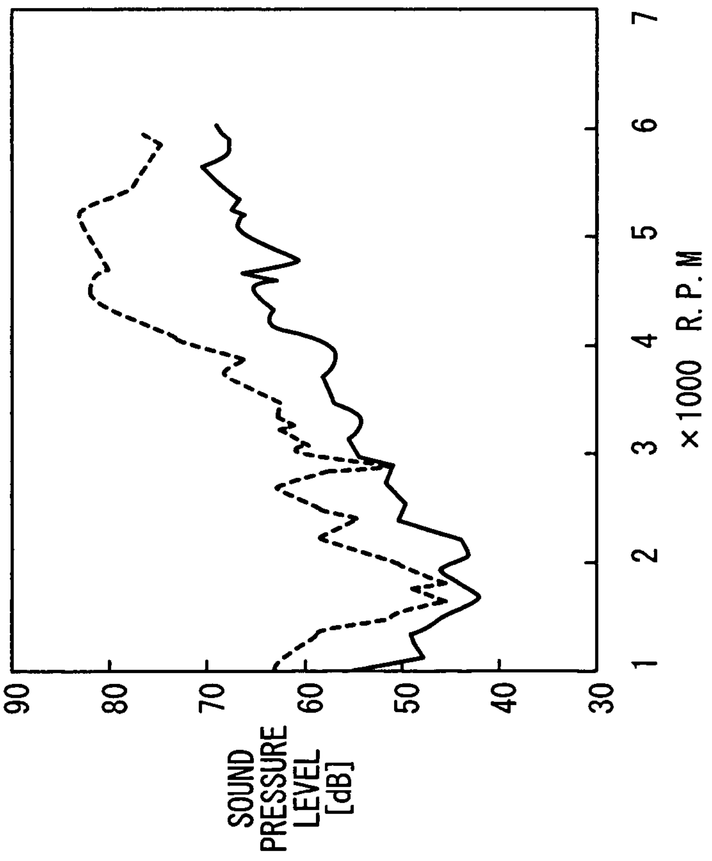
FIGS. 12A and 12B are diagrams showing results of the muffled-sound canceling process of the active vibratory noise control apparatus according to the embodiment of the present invention.

Using the reference cosine wave signal, the reference sine wave signal, and the first and second reference signals thus obtained, canceling vibratory noise (vibratory noise canceling signal) was generated through the adaptive notch filters 14, 15, and vibratory noise including muffled sounds was canceled by the canceling vibratory noise (vibratory noise canceling signal). The results of the vibratory noise cancellation as plotted against rotational speeds of the engine output shaft are indicated by the solid-line curve in FIG. 12A. The muffled sounds which were not canceled are indicated by the broken-line curve in FIG. 12A. A comparison between the solid-line curve and the broken-line curve in FIG. 12A clearly shows that muffled sounds were sufficiently canceled by the active vibratory noise control apparatus 10.

Figure 12B:
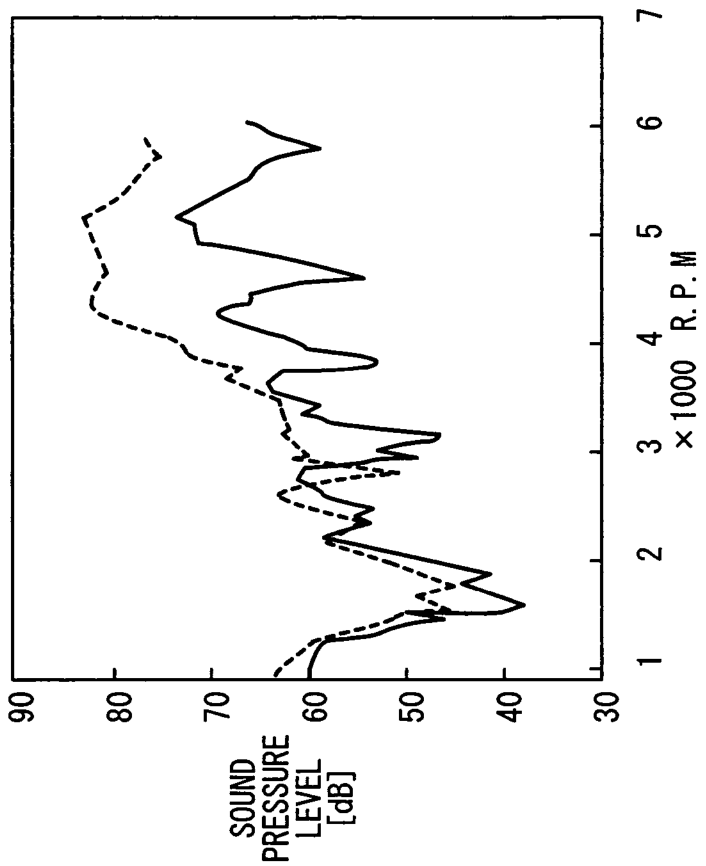

The solid-line curve shown in FIG. 12B was plotted when the signal transfer characteristics were modeled with the FIR filter described in Japanese Laid-Open Patent Publication No. 1-501344 (PCT application), and muffled sounds were canceled by a muffled sound canceling signal generated by the one-speaker, one-microphone active vibratory noise control apparatus with the adaptive FIR filter. The broken-line curve shown in FIG. 12B was plotted when muffled sounds were not canceled.

It can be seen from the foregoing that good canceling results are achieved by modeling the signal transfer characteristics using the address shift values and canceling muffled sounds using the first and second reference signals and the adaptive notch filters.

With respect to the amount of calculations required for the active vibratory noise control apparatus 10 to model the signal transfer characteristics using the address shift values and cancel muffled sounds using the adaptive notch filters, two additions and two multiplications may be made in order to determine the reference signals expressed by the equation (14) in each adaptive processing cycle, and four multiplications and four additions may be made for an adaptive processing sequence using the LSM algorithm calculations according to the equations (16-1), (16-2). Therefore, the number of calculations required by the active vibratory noise control apparatus 10 is small.

With the active vibratory noise control apparatus disclosed in Japanese Laid-Open Patent Publication No. 1-501344 (PCT application), since it performs convolutional calculations, if the number of taps of the FIR filter which models the signal transfer characteristics is j=128 and the number of taps of the adaptive FIR filter is i=64, then 128 multiplications and 127 additions need to be made to determine reference signals, 193 multiplications and 192 additions need to be made for an adaptive processing sequence, and 64 multiplications and 63 additions need to be made for outputting the results. Because of the large number of calculations required, the active vibratory noise control apparatus cannot be implemented by an inexpensive microcomputer, but needs to be implemented by a DSP (digital signal processor), and is hence expensive to manufacture.

As shown in FIG. 9E, the gain in the measured signal transfer characteristics in the reference signal frequency range from 30 Hz to 41 Hz ranges from −30 dB to −20 dB, which is smaller than a gain range in another reference signal frequency range from 42 Hz to 230 Hz. Therefore, the value of the gain α varies in a large range in FIG. 9E. If multiplications are made with the gain values shown in FIG. 9E by a microcomputer whose calculated results have 8 bits, then since an inexpensive 8-bit microcomputer generally does not perform calculations with an exponential representation of values, figure canceling occurs because of the number of effective figures while the inexpensive 8-bit microcomputer is performing a process of calculating first and second reference numbers multiplied by the gain or an LMS processing sequence, resulting in a reduction in the accuracy with which to calculate the first and second reference signals or the filter coefficients of the first and second adaptive notch filers 14, 15, and hence in a reduction in the sound silencing capability.

As described above in relation to the equations (16-1), (16-2), since the gain α is substituted for the step size parameter μ' at each control frequency, a small value of the gain α is equivalent to a small value of the step size parameter μ', and hence the speed at which the filter coefficients are converged is lowered, resulting in poorer responsiveness.

A process of increasing the calculating accuracy and converging speed in the low frequency band by changing only the gain, but not changing the measured phase lag (ϕ) in the low frequency range from 30 Hz to 41 Hz, based on the idea that α(f) which reflects the gain of the signal transfer characteristics is an adjusting element at each control frequency, as described above in relation to the equations (14), (15-1), (15-2), will be described below.

The gain in the measured signal transfer characteristics in the reference wave signal frequency range from 30 Hz to 41 Hz is increased to a value close to the gain at the reference wave signal frequency of 42 Hz, e.g., −10 dB, as shown in FIGS. 13A and 13E, rather than FIGS. 9A and 9E, and first and second reference signals are determined. The phase lag (ϕ) used in this calculating process is not corrected as shown in FIGS. 13B and 13C, but is the measured phase lag (ϕ) as shown in FIGS. 13B and 13C like the one shown in FIGS. 9B and 9C. Therefore, the value of the gain α has a small variation range, the accuracy with which to calculate gain multiplications with the 8-bit microcomputer in the frequency range from 30 Hz to 41 Hz is about the same as the accuracy with which to calculate gain multiplications in the frequency range from 42 Hz to 230 Hz, and the converging speed in the reference signal frequency range from 30 Hz to 41 Hz is increased. The memory 23 stores address shifts shown in FIG. 13D corresponding to phase lags shown in FIG. 13C.

FIG. 13A shows the measured and corrected gains (the broken-line curve shows the measured gain), and FIG. 13B shows the measured phase lag (ϕ). Since the measured phase lag (ϕ) is used as the phase lag (ϕ), it does not affect the cancellation of vibratory noise including muffled sounds.

The above instance of correcting the gain α may be expanded to make the value of the gain α an upper limit value based on the number of bits of the microcomputer used in the calculations in the full frequency range. In this manner, the accuracy of the calculations can be increased.

Specifically, the gain may be set to 0 dB to set the gain α to α=127. FIG. 14A shows the corrected gain (the broken-line curve shows the measured gain), and FIG. 14B shows the measured phase lag (ϕ). FIGS. 14C and 14E show tables of values of the measured phase lag (ϕ) and the corrected gain α. In this example, the calculating accuracy is prevented from varying due to the varying values of the gain α by making the gain constant in the full frequency range, and the calculating accuracy is increased and the converging speed is also increased by setting the gain to an upper limit value that is determined by the number of bits of the computer used for calculations. The memory 23 stores address shifts shown in FIG. 14D corresponding to phase lags shown in FIG. 14C.

A first modified system in which the active vibratory noise control apparatus 10 is incorporated in a motor vehicle 51 will be described below with reference to FIG. 15.

Figure 15:
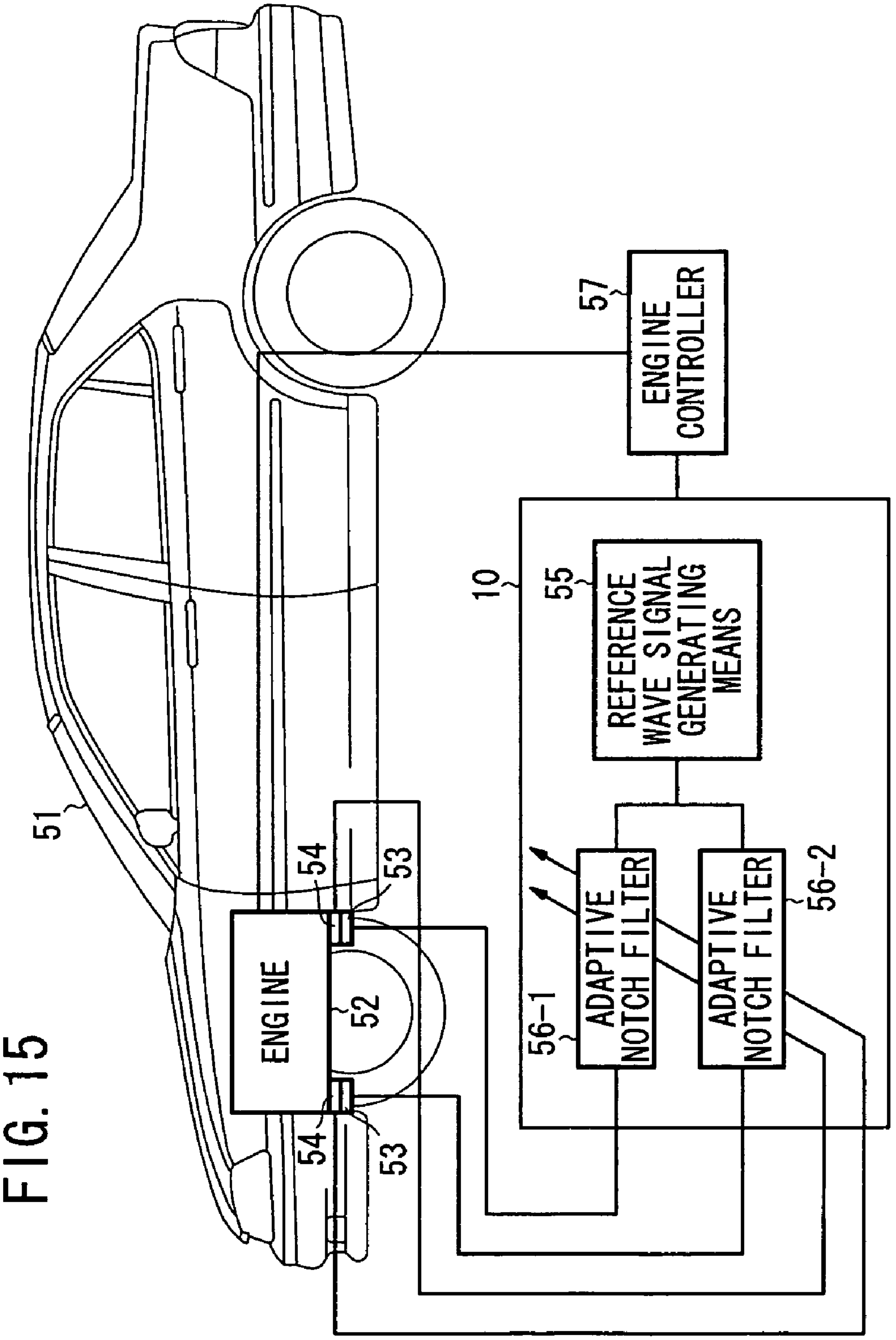
FIG. 15 is a block diagram of a first modified system for measuring signal transfer characteristics of the active vibratory noise control apparatus according to the embodiment of the present invention.

FIG. 15 schematically shows an arrangement for canceling vibratory noise produced by the engine with engine mounts.

In the first modified system, self-expandable/contractible engine mounts 53 for supporting the engine 52 of the motor vehicle 51 are used instead of the speaker 17, and vibration detecting sensors 54 disposed near the engine mounts 53 are used instead of the microphone 18.

In FIG. 15, the active vibratory noise control apparatus 10 comprises an 8-bit microcomputer, for example, and is represented by a reference wave signal generating means 55 and adaptive notch filters 56-1, 56-2.

Engine pulses output from an engine controller 57 which controls the engine 52 of the motor vehicle 51 are input to the active vibratory noise control apparatus 10 which coacts with the engine mounts 53 and the vibration detecting sensors 54. The adaptive notch filters 56-1, 56-2 whose filter coefficients are adaptively controlled to minimize output signals from the vibration detecting sensors 54, i.e., to minimize an error signal, apply output signals to actuate the engine mounts 53 separately from each other to cancel out vibratory noise of the engine 52 to suppress vibratory noise and muffled sounds in the passenger compartment. The process of canceling vibratory noise and muffled sounds has already been described above with respect to the active vibratory noise control apparatus 10.

A second modified system in which the active vibratory noise control apparatus 10 is incorporated in a motor vehicle 61 will be described below with reference to FIG. 16.

Figure 16:
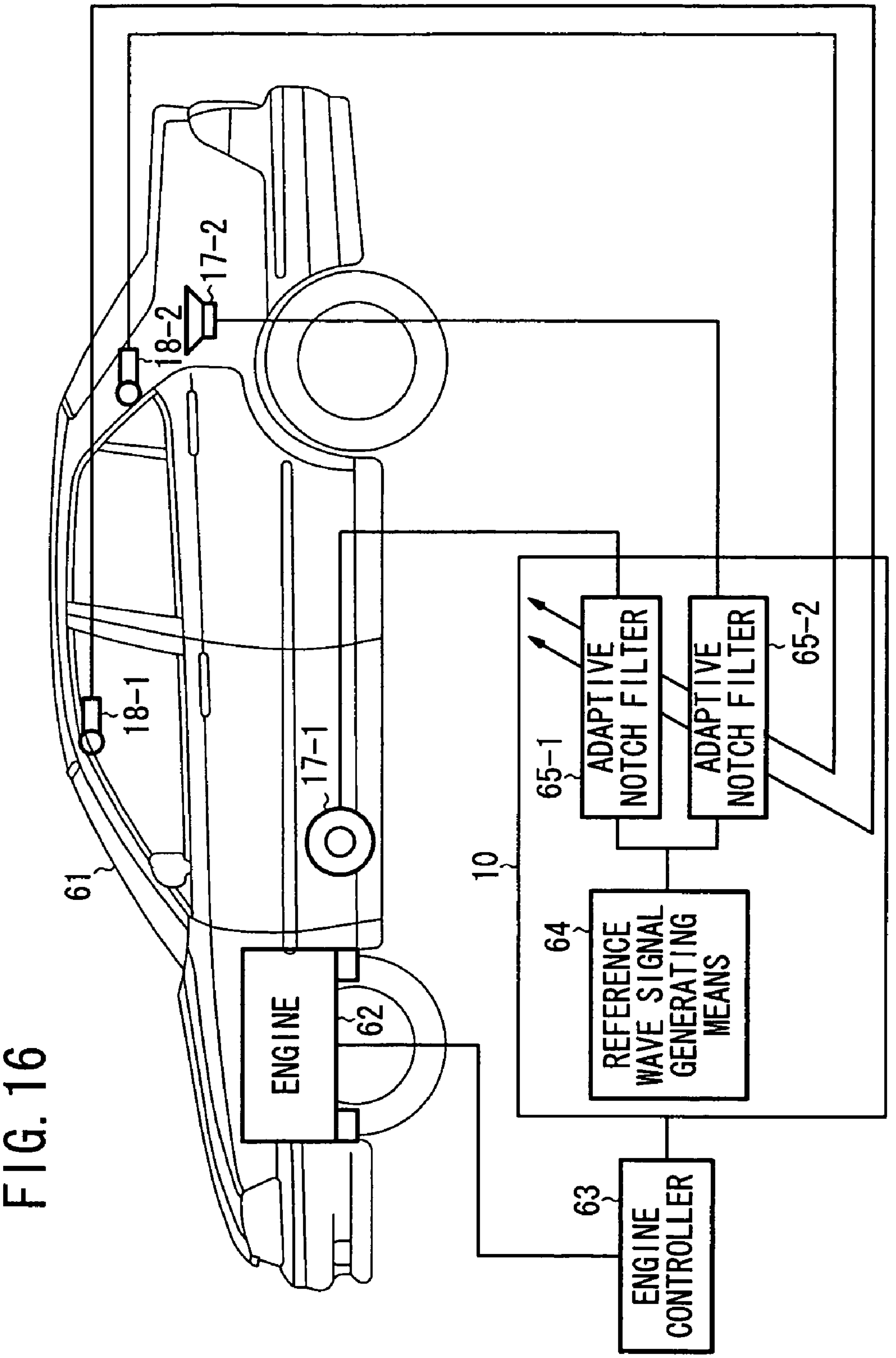
FIG. 16 is a block diagram of a second modified system for measuring signal transfer characteristics of the active vibratory noise control apparatus according to the embodiment of the present invention.

FIG. 16 schematically shows an arrangement for canceling muffled sounds in the passenger compartment of the motor vehicle 61 with the active vibratory noise control apparatus 10 which has two microphones.

In FIG. 16, the active vibratory noise control apparatus 10 comprises an 8-bit microcomputer, for example, and is represented by a reference wave signal generating means 64 and adaptive notch filters 65-1, 65-2 for ease.

A speaker 17-2 is disposed in a given position in a tray behind the rear seats in the motor vehicle 61, and another speaker 17-1 is disposed in a given position on a lower portion of a door near a front seat. A microphone 18-2 is disposed on a ceiling portion of the passenger compartment which faces the back of the rear seat of the motor vehicle 61, and another microphone 18-1 is disposed on a central portion facing the front seat of the motor vehicle 61.

Engine pulses output from an engine controller 63 which controls an engine 62 of the motor vehicle 61 are input to the active vibratory noise control apparatus 10 which coacts with the speakers 17-1, 17-2 and the microphones 18-1, 18-2. The adaptive notch filters 65-1, 65-2 which are adaptively controlled to minimize output signals from the microphones 18-1, 18-2 apply output signals to energize the speakers 17-1, 17-2 to cancel vibratory noise in the passenger compartment of the motor vehicle 61. The process of canceling vibratory noise has already been described above with respect to the active vibratory noise control apparatus 10.

First and second reference signals for updating the filter coefficients of the adaptive notch filter 65-1 are generated based on the phase lag of the signal transfer characteristics between the speaker 17-1 and the microphone 18-1 and the phase lag of the signal transfer characteristics between the speaker 17-1 and the microphone 18-2. The speaker 17-1 is energized by an output signal from the adaptive notch filter 65-1 which is adaptively controlled to minimize error signals from the microphones 18-1, 18-2 in response to the error signals from the microphones 18-1, 18-2 and the reference signals. First and second reference signals for updating the filter coefficients of the adaptive notch filter 65-2 are generated based on the phase lag of the signal transfer characteristics between the speaker 17-2 and the microphone 18-1 and the phase lag of the signal transfer characteristics between the speaker 17-2 and the microphone 18-2. The speaker 17-2 is energized by an output signal from the adaptive notch filter 65-2 which is adaptively controlled to minimize error signals from the microphones 18-1, 18-2 in response to the error signals from the microphones 18-1, 18-2 and the reference signals. In this manner, muffled sounds in the passenger compartment are canceled.

In the above description, the memory 19 stores waveform data representing instantaneous value data of a sine wave at respective divided positions where one period of the sine wave is divided by a predetermined number, and addresses of the memory 19 are designated at address intervals based on the control frequency of a signal output from the frequency detecting circuit 11 and at predetermined time intervals, so that the waveform data is read as a reference sine wave signal from the designated addresses of the memory 19. However, the memory 19 may store waveform data representing instantaneous value data of a cosine wave rather than a sine wave, and addresses of the memory 19 may be designated at address intervals based on the control frequency of a signal output from the frequency detecting circuit 11 and at predetermined time intervals, so that the waveform data is read as a reference cosine wave signal from the designated addresses of the memory 19.

Addresses of the memory 19 may be successively designated at time intervals based on the control frequency of a signal output from the frequency detecting circuit 11, so that the waveform data is read as a reference wave signal from the designated addresses of the memory 19.

With the active vibratory noise control apparatus according to the present invention, address shift values based on the phase characteristics of the signal transfer characteristics from the vibratory noise canceling means to the error signal detecting means are stored in advance in the corrective data storage means depending on the frequency of a reference wave signal, and waveform data read from addresses that are produced by shifting address data for reading a reference cosine wave signal and a reference sine wave signal from the waveform data storage means by referring to the frequency of the reference wave signal, by an address shift value read from the corrective data storage means, are used as first and second reference signals. The active vibratory noise control apparatus can optimally model the signal transfer characteristics and cancel generated vibratory noise through a reduced number of calculations with a sufficient converging capability.

Although certain preferred embodiments of the present invention have been shown and described in detail, it should be understood that various changes and modifications may be made therein without departing from the scope of the appended claims.

What is claimed is:

1. An apparatus for actively controlling vibratory noise, comprising:

reference wave signal generating means for outputting a reference wave signal having a harmonic frequency selected from frequencies of vibration or noise generated from a vibratory noise source;

an adaptive notch filter for outputting a control signal based on said reference wave signal in order to cancel vibratory noise;

vibratory noise canceling means for generating a vibratory noise canceling sound based on said control signal;

error signal detecting means for outputting an error signal based on a difference between said vibration or noise and said vibratory noise canceling sound;

phase correcting means for correcting said reference wave signal into a reference signal based on a measured value representing phase characteristics with respect to a frequency of said reference wave signal in transfer characteristics from said vibratory noise canceling means to said error signal detecting means, and outputting said reference signal;

filter coefficient updating means for sequentially updating a filter coefficient of said adaptive notch filter in order to minimize said error signal based on said error signal and said reference signal, wherein said reference wave signal generating means has waveform data storage means for storing waveform data representing instantaneous value data at respective divided positions where one period of a sine wave or a cosine wave is divided by a predetermined number, and successively reads said waveform data from said waveform data storage means per sampling to generate said reference wave signal, wherein said phase correcting means has measured data storage means for storing said measured value with respect to said frequency of said reference wave signal, and said phase correcting means reads said measured value from said measured data storage means by referring to said frequency of said reference wave signal, shifts an address at which said reference wave signal generating means reads said waveform data from said waveform data storage means, by said measured value, and reads said waveform data from said shifted address of said waveform data storage means as said reference signal; and a gain setting unit for correcting a gain of the read-out reference signal, wherein in gain characteristics measured with respect to said frequency of said reference wave signal in transfer characteristics from said vibratory noise canceling means to said error signal detecting means, corrective gain characteristics are set to said gain setting unit by increasing the gain at a frequency where the measured gain characteristics drop, and wherein the read-out reference signal from said phase correcting means is corrected based on the corrective gain characteristics without correcting the measured phase characteristics at the frequency where the measured gain characteristics drop, and then supplied to said filter coefficient updating means as said reference signal.

2. An apparatus for actively controlling vibratory noise, comprising:

reference wave signal generating means for outputting a reference sine wave signal and a reference cosine wave signal having a harmonic frequency selected from frequencies of vibration or noise generated from a vibratory noise source;

a first adaptive notch filter for outputting a first control signal based on said reference cosine wave signal and a second adaptive notch filter for outputting a second control signal based on said reference sine wave signal in order to cancel generated vibratory noise;

vibratory noise canceling means for generating a vibratory noise canceling sound based on a sum signal representing the sum of said first control signal and said second control signal;

error signal detecting means for outputting an error signal based on a difference between said vibration or noise and said vibratory noise canceling sound;

phase correcting means for correcting said reference cosine wave signal into a first reference signal and correcting said reference sine wave signal into a second reference signal, based on a measured value representing phase characteristics with respect to a frequency of each of said reference cosine wave signal and said reference sine wave signal in transfer characteristics from said vibratory noise canceling means to said error signal detecting means, and outputting said first reference signal and said second reference signal, filter coefficient updating means for sequentially updating a filter coefficient of said first adaptive notch filter and a filter coefficient of said second adaptive notch filter in order to minimize said error signal based on said error signal, said first reference signal, and said second reference signal, wherein said reference wave signal generating means has waveform data storage means for storing waveform data representing instantaneous value data at respective divided positions where one period of a cosine wave is divided by a predetermined number, and said reference wave signal generating means successively reads said waveform data from said waveform data storage means per sampling to generate said reference cosine wave signal, and successively reads said waveform data from addresses of said waveform data storage means which are produced by shifting addresses at which said reference cosine signal is read, by a quarter of said period, to generate said reference sine wave signal, wherein said phase correcting means has measured data storage means for storing said measured value with respect to said frequency of said reference wave signal, and said phase correcting means reads said measured value from said measured data storage means by referring to said frequency of said reference wave signal, shifts an address at which said reference wave signal generating means reads said waveform data as said reference cosine wave signal from said waveform data storage means, by said measured value, reads said waveform data from said shifted address of said waveform data storage means as said first reference signal, shifts an address at which said reference wave signal generating means reads said waveform data as said reference sine wave signal from said waveform data storage means, by said measured value, and reads said waveform data from said shifted address of said waveform data storage means as said second reference signal; and a gain setting unit for correcting gains of the first reference signal and the second reference signal, wherein in gain characteristics measured with respect to said frequency of said reference wave signal in transfer characteristics from said vibratory noise canceling means to said error signal detecting means, corrective gain characteristics are set to said gain setting unit by increasing the gain at a frequency where the measured gain characteristics drop, and wherein the first reference signal and the second reference signal are corrected based on the corrective gain characteristics without correcting the measured phase characteristics of the first reference signal and the second reference signal at the frequency where the measured gain characteristics drop, and then supplied to said filter coefficient updating means as said first reference signal and the second reference signal.

3. An apparatus for actively controlling vibratory noise, comprising:

reference wave signal generating means for outputting a reference sine wave signal and a reference cosine wave signal having a harmonic frequency selected from frequencies of vibration or noise generated from a vibratory noise source;

a first adaptive notch filter for outputting a first control signal based on said reference cosine wave signal and a second adaptive notch filter for outputting a second control signal based on said reference sine wave signal in order to cancel generated vibratory noise;

vibratory noise canceling means for generating a vibratory noise canceling sound based on a sum signal representing the sum of said first control signal and said second control signal;

error signal detecting means for outputting an error signal based on a difference between said vibration or noise and said vibratory noise canceling sound;

phase correcting means for correcting said reference cosine wave signal into a first reference signal and correcting said reference sine wave signal into a second reference signal, based on a measured value representing phase characteristics with respect to a frequency of each of said reference cosine wave signal and said reference sine wave signal in transfer characteristics from said vibratory noise canceling means to said error signal detecting means, and outputting said first reference signal and said second reference signal; and filter coefficient updating means for sequentially updating a filter coefficient of said first adaptive notch filter and a filter coefficient of said second adaptive notch filter in order to minimize said error signal based on said error signal, said first reference signal, and said second reference signal, wherein said reference wave signal generating means has waveform data storage means for storing waveform data representing instantaneous value data at respective divided positions where one period of a sine wave is divided by a predetermined number, and said reference wave signal generating means successively reads said waveform data from said waveform data storage means per sampling to generate said reference sine wave signal, and successively reads said waveform data from addresses of said waveform data storage means which are produced by shifting addresses at which said reference sine signal is read, by a quarter of said period, to generate said reference cosine wave signal, wherein said phase correcting means has measured data storage means for storing said measured value with respect to said frequency of said reference wave signal, and said phase correcting means reads said measured value from said measured data storage means by referring to said frequency of said reference wave signal, shifts an address at which said reference wave signal generating means reads said waveform data as said reference sine wave signal from said waveform data storage means, by said measured value, reads said waveform data from said shifted address of said waveform data storage means as said second reference signal, shifts an address at which said reference wave signal generating means reads said waveform data as said reference cosine wave signal from said waveform data storage means, by said measured value, and reads said waveform data from said shifted address of said waveform data storage means as said first reference signal; and a gain setting unit for correcting gains of the first reference signal and the second reference signal;

wherein in gain characteristics measured with respect to said frequency of said reference wave signal in transfer characteristics from said vibratory noise canceling means to said error signal detecting means, corrective gain characteristics are set to said gain setting unit by increasing the gain at a frequency where the measured gain characteristics drop; and wherein the first reference signal and the second reference signal are corrected based on the corrective gain characteristics without correcting the measured phase characteristics of the first reference signal and the second reference signal at the frequency where the measured gain characteristics drop, and then supplied to said filter coefficient updating means as said first reference signal and the second reference signal.

* * * * *